US010022687B2

(12) United States Patent
Vogt et al.

(10) Patent No.: US 10,022,687 B2
(45) Date of Patent: Jul. 17, 2018

(54) VACUUM MIXING DEVICE WITH OPERATING ELEMENT AND PUMP FOR MIXING POLYMETHYLMETHACRYLATE BONE CEMENT

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 65 days.

(21) Appl. No.: 15/371,336

(22) Filed: Dec. 7, 2016

(65) Prior Publication Data
US 2017/0157578 A1 Jun. 8, 2017

(30) Foreign Application Priority Data
Dec. 7, 2015 (DE) ........................ 10 2015 121 274

(51) Int. Cl.
*B01F 3/14* (2006.01)
*B01F 13/06* (2006.01)
(Continued)

(52) U.S. Cl.
CPC .......... *B01F 13/06* (2013.01); *A61B 17/8833* (2013.01); *A61L 24/06* (2013.01);
(Continued)

(58) Field of Classification Search
None
See application file for complete search history.

(56) References Cited

U.S. PATENT DOCUMENTS 3,623,474 A * 11/1971 Heilman .......... A61M 5/14546
600/432
3,701,345 A * 10/1972 Heilman ................ A61B 6/481
128/DIG. 1
(Continued)

FOREIGN PATENT DOCUMENTS

DE 3 640 279 A1 6/1987
DE 200 05 333 U1 7/2001
(Continued)

OTHER PUBLICATIONS

European Search Report corresponds to European Application No. 16202439.2, dated May 4, 2017.

*Primary Examiner* — Peter A Salamon
(74) *Attorney, Agent, or Firm* — Norris McLaughlin & Marcus P.A.

(57) ABSTRACT

A vacuum mixing device for mixing PMMA bone cement from a monomer liquid and a cement powder, the vacuum mixing device comprising at least one cartridge comprising an evacuable interior for mixing of the bone cement, a mixing device for mixing the content in the interior of the at least one cartridge, which is arranged movably in the interior, a receptacle for receiving a separate container containing the monomer liquid or comprising an integrated container containing the monomer liquid, an opening device, which is arranged in the region of the receptacle in a manner movable relative to the receptacle so that, by moving the opening device, a separate container arranged in the receptacle is openable by means of the opening device, or the opening device is arranged in the region of the integrated container in a manner movable relative to the integrated container so that, by moving the opening device, the integrated container is openable by means of the opening device, a pump, in which a movable plunger for generating a negative pressure is arranged and delimits a pump chamber (Continued)

of the pump, and a connection line, which connects the interior of the at least one cartridge to the pump chamber of the pump, wherein the vacuum mixing system comprises an operating element that is operatable from outside, wherein the plunger in the pump is movable manually by means of the operating element, and wherein the opening device is movable relative to the receptacle or relative to the integrated container by means of the same operating element, and the mixing device in the interior of the cartridge is movable by means of the same operating element in order to mix the content in the interior of the cartridge.

25 Claims, 8 Drawing Sheets

(51) Int. Cl.
  *B01F 3/12* (2006.01)
  *B01F 7/16* (2006.01)
  *B01F 15/02* (2006.01)
  *A61L 24/06* (2006.01)
  *A61B 17/88* (2006.01)

(52) U.S. Cl.
  CPC ............. *B01F 3/1228* (2013.01); *B01F 3/14* (2013.01); *B01F 7/16* (2013.01); *B01F 15/0206* (2013.01); *B01F 15/0258* (2013.01); *B01F 15/0278* (2013.01); *A61B 2017/8838* (2013.01); *B01F 2003/1257* (2013.01); *B01F 2215/0029* (2013.01)

(56) References Cited

U.S. PATENT DOCUMENTS

| | | | | |
|---|---|---|---|---|
| 3,752,364 | A * | 8/1973 | De Vries | A47G 19/183 222/131 |
| 4,322,022 | A * | 3/1982 | Bergman | B05C 17/0103 222/327 |
| 4,479,781 | A * | 10/1984 | Herold | A61C 9/0026 222/390 |
| 4,560,352 | A * | 12/1985 | Neumeister | A61C 9/0026 222/390 |
| 4,671,263 | A | 6/1987 | Draenert | |
| 4,758,096 | A * | 7/1988 | Gunnarsson | B01F 13/06 366/139 |
| 4,808,184 | A * | 2/1989 | Tepic | A61L 24/06 215/DIG. 8 |
| 4,973,168 | A | 11/1990 | Chan | |
| 5,100,241 | A | 3/1992 | Chan | |
| 5,137,514 | A * | 8/1992 | Ryan | A61M 25/1018 604/100.01 |
| 5,341,958 | A * | 8/1994 | Bayat | B05C 17/0103 222/333 |
| 5,344,232 | A | 9/1994 | Nelson et al. | |
| 5,505,538 | A * | 4/1996 | Earle | B01F 13/0016 366/139 |
| 5,516,135 | A * | 5/1996 | Christenson | B62D 61/12 180/24.02 |
| 5,551,778 | A | 9/1996 | Hauke et al. | |
| 5,586,821 | A | 12/1996 | Bonitati et al. | |
| 5,588,745 | A * | 12/1996 | Tanaka | A61B 17/8833 206/222 |
| 5,624,184 | A | 4/1997 | Chan | |
| 5,997,544 | A | 12/1999 | Nies et al. | |
| 6,033,105 | A | 3/2000 | Barker et al. | |
| 6,042,262 | A * | 3/2000 | Hajianpour | A61B 17/8822 366/139 |
| 6,176,607 | B1 * | 1/2001 | Hajianpour | A61B 17/8822 366/139 |
| 6,571,992 | B2 * | 6/2003 | Pierson | B65D 83/0011 222/390 |
| 6,675,992 | B2 * | 1/2004 | Schumann | F16N 11/08 184/105.2 |
| 6,709,149 | B1 | 3/2004 | Tepic | |
| 7,008,433 | B2 * | 3/2006 | Voellmicke | A61B 17/8822 222/256 |
| 7,025,226 | B2 * | 4/2006 | Ramey | A61M 5/1456 222/1 |
| 8,021,037 | B2 * | 9/2011 | Krueger | A61B 17/8822 222/290 |
| 8,132,959 | B2 * | 3/2012 | Smit | A61B 17/8833 206/222 |
| 8,356,927 | B1 * | 1/2013 | Lordi | B01F 5/0685 366/130 |
| 8,662,736 | B2 | 3/2014 | Vogt et al. | |
| 9,163,749 | B2 * | 10/2015 | Donovan | A61B 17/8822 |
| 9,204,914 | B2 * | 12/2015 | Chabansky | B01F 13/002 |
| 9,480,955 | B2 * | 11/2016 | Sasaki | |
| 2002/0191487 | A1 * | 12/2002 | Sand | B01F 7/0005 366/252 |
| 2003/0021180 | A1 | 1/2003 | Wahlig et al. | |
| 2004/0196735 | A1 * | 10/2004 | Barker | A61B 17/8833 366/139 |
| 2005/0222538 | A1 * | 10/2005 | Embry | A61B 17/8816 604/181 |
| 2006/0256646 | A1 * | 11/2006 | Bidoia | A61B 17/8827 366/139 |
| 2008/0116224 | A1 * | 5/2008 | Krueger | A61B 17/8822 222/192 |
| 2009/0264816 | A1 * | 10/2009 | Johnson | A61B 17/8827 604/82 |
| 2010/0329074 | A1 * | 12/2010 | Vogt | A61B 17/8825 366/190 |
| 2013/0135957 | A1 * | 5/2013 | Vogt | B29B 7/12 366/75 |
| 2015/0367301 | A1 | 12/2015 | Vogt | |

FOREIGN PATENT DOCUMENTS

| | | |
|---|---|---|
| DE | 69812726 T2 | 2/2004 |
| DE | 10 2009 031 178 B3 | 9/2010 |
| DE | 10 2014 108 569 B3 | 10/2015 |
| EP | 0 692 229 A1 | 1/1996 |
| EP | 1 005 901 A2 | 6/2000 |
| EP | 1 016 452 A2 | 7/2000 |
| EP | 1 020 167 A2 | 7/2000 |
| EP | 1886647 A1 | 2/2008 |
| WO | 94 26403 A1 | 11/1994 |
| WO | 99 67015 A1 | 12/1999 |
| WO | 00/35506 A1 | 6/2000 |

* cited by examiner

VACUUM MIXING DEVICE WITH OPERATING ELEMENT AND PUMP FOR MIXING POLYMETHYLMETHACRYLATE BONE CEMENT

This application claims foreign priority benefit under 35 U.S.C. 119 of German Application No. DE 10 2015 121 274.9 filed Dec. 7, 2015.

FIELD OF THE DISCLOSURE

The invention relates to a vacuum mixing device for the mixing of polymethylmethacrylate bone cement (PMMA bone cement) from two starting components, in particular for the mixing of a medical bone cement, and for storage of the starting components. The invention further relates to a method for the mixing of polymethylmethacrylate bone cement.

Accordingly, the subject matter of the invention is a vacuum mixing device for the storage, mixing, and, if applicable, dispensing of polymethylmethacrylate bone cement. The invention further relates to a method for the transferring of monomer liquid into the vacuum mixing device and to a method for the mixing of the components of polymethylmethacrylate bone cement under vacuum or at negative pressure.

BACKGROUND

Polymethylmethacrylate (PMMA) bone cements are based on the pioneering work of Sir Charnley. PMMA bone cements consist of a liquid monomer component and a powder component. The monomer component generally contains the monomer, methylmethacrylate, and an activator (N,N-dimethyl-p-toluidine) dissolved therein. The powder component, which is also referred to as bone cement powder, comprises one or more polymers, which are produced on the basis of methylmethacrylate and comonomers, such as styrene, methylacrylate or similar monomers by means of polymerisation, preferably by suspension polymerisation. The bone cement powder additionally comprises a radiopaquer and the initiator dibenzoylperoxide. During the mixing of powder component and monomer component, swelling of the polymers of the powder component in the methylmethacrylate generates a dough that can be shaped plastically and is the actual bone cement. During the mixing of powder component and monomer component, the activator, N,N-dimethyl-p-toluidine, reacts with dibenzoylperoxide while forming radicals. The radicals thus formed trigger the radical polymerisation of the methylmethacrylate. Upon advancing polymerisation of the methylmethacrylate, the viscosity of the cement dough increases until the cement dough solidifies.

Methylmethacrylate is the monomer used most commonly in polymethylmethacrylate bone cements. Redox initiator systems usually consist of peroxides, accelerators and, if applicable, suitable reducing agents. Radicals are formed only if all ingredients of the redox initiator systems interact. For this reason, the ingredients of the redox initiator system in the separate starting components are arranged appropriately such that these cannot trigger a radical polymerisation. The starting components are stable during storage provided their composition is adequate. Only when the two starting components are mixed to produce a cement dough do the ingredients of the redox initiator system, previously stored separately in the two pastes, liquids or powders, react with each other, forming radicals which trigger the radical polymerisation of the at least one monomer. The radical polymerisation then leads to the formation of polymers while consuming the monomer, as a result of which the cement dough is cured.

PMMA bone cements can be mixed by mixing the cement powder and the monomer liquid in suitable mixing beakers with the aid of spatulas. One disadvantage of said procedure is that air inclusions may be present in the cement dough thus formed and can cause destabilisation of the bone cement later on.

For this reason, it is preferred to mix bone cement powder and monomer liquid in mixing devices with vacuum sources, since mixing in a vacuum removes air inclusions from the cement dough to a large extent and thus achieves optimal cement quality. Bone cements mixed in a vacuum or at negative pressure have clearly reduced porosity and thus show improved mechanical properties. A large number of vacuum cementing systems have been disclosed of which the following shall be listed for exemplary purposes: U.S. Pat. No. 6,033,105 A, U.S. Pat. No. 5,624,184 A, U.S. Pat. No. 4,671,263 A, U.S. Pat. No. 4,973,168 A, U.S. Pat. No. 5,100,241 A, WO 99/67015 A1, EP 1 020 167 A2, U.S. Pat. No. 5,586,821 A, EP 1 016 452 A2, DE 36 40 279 A1, WO 94/26403 A1, WO 00/35506 A1, EP 1 005 901 A2, U.S. Pat. No. 5,344,232 A. In the vacuum cementing systems thus specified, there is a need to connect an external vacuum pump to generate the negative pressure. These are generally operated by compressed air utilising the Venturi principle. The compressed air required for operation of the vacuum pumps is supplied either by stationary compressed air facilities or by electrically-operated compressors. In addition, it is also feasible to use electrically-operated vacuum pumps to generate vacuum.

Cementing systems in which both the cement powder and the monomer liquid are already packed in separate compartments of the mixing systems and are mixed with each other in the cementing system only right before application of the cement, are a development of cementing technology. Such full-prepacked mixing systems were proposed through EP 0 692 229 A1, DE 10 2009 031 178 B3, U.S. Pat. No. 5,997,544 A, U.S. Pat. No. 6,709,149 B1, DE 698 12 726 T2 and U.S. Pat. No. 5,588,745 A. Said mixing systems also require an external vacuum source. In this context, the patent DE 10 2009 031 178 B3 discloses a vacuum mixing device having a two-part dispensing plunger that can also be used for a vacuum mixing device according to the invention. Here, a combination of a gas-permeable sterilisation plunger and a gas-impermeable sealing plunger is used.

If vacuum mixing devices are used for cementing, external vacuum pumps need to be provided. Said vacuum pumps are expensive and need to be cleaned after use. Moreover, vacuum hoses for connecting the vacuum pumps to the vacuum mixing devices are required. Said vacuum hoses need to be enclosed with the vacuum mixing devices. Accordingly, prior to the mixing using a vacuum mixing device, the vacuum pump needs first to be set up in the operating theatre (OP theatre) and must be connected to an energy source, such as compressed air, or to an electrical power source. Then, the vacuum pump is connected to the vacuum mixing device by means of a vacuum hose. Said installation steps take up costly OP time and are potentially error-prone. The vacuum pump and connecting lines to the vacuum mixing device and to external energy sources and supply lines take up space and constitute potential tripping hazards and obstacles that can disturb the often hectic procedure during surgery.

A further interesting concept has been proposed through EP 1 886 647 A1. Here, the cement powder is stored in an evacuated cartridge and the monomer liquid is situated in a separate container. The cartridge, which is kept at a negative pressure, being opened causes the monomer liquid to be aspirated into the cartridge without any ingress of air. A bone cement dough free of air inclusions is thus produced. Said concept requires the cartridge to remain closed in vacuum-tight manner during the storage before use such that no non-sterile air can enter into the cartridge. For this purpose, the cartridge must be sealed in a stable hermetic manner. Accordingly, one associated disadvantage is that the design is quite elaborate and that the content in the cartridge cannot be mixed by an externally-operated mixing system after aspiration of the monomer since a feedthrough for a mixing bar or for a mixing tube would not readily be permanently vacuum-tight.

SUMMARY OF THE DISCLOSURE

Accordingly, it is the object of the invention to overcome the disadvantages of the prior art. Specifically, the disadvantages of the known vacuum mixing devices as full-prepacked systems having an external vacuum source are to be overcome without having to maintain a negative pressure over a long period of time. It is the object of the invention, specifically, to develop a vacuum mixing device in which a negative pressure is generated only just before the cement components are being mixed. The device is to be simplified to the greatest possible extent and is to allow a negative pressure with respect to the surrounding atmosphere to be generated, at least once, in a cement cartridge. Moreover, it can be advantageous that the vacuum mixing device is capable of enabling a transfer of monomer liquid from a monomer container into a cartridge filled with cement powder. Moreover, a method is then to be provided that enables a monomer transfer and a vacuum mixing in full-prepacked mixing devices. Moreover, it is to be possible to manufacture the vacuum mixing device to be developed mainly from inexpensive plastics material.

A further object of the invention is to develop a simple, closed prepacked mixing device with which polymethylmethacrylate bone cement powder and monomer liquid can be stored in separate compartments, and then mixed. It is to be possible to transfer the monomer liquid into the cement powder just before the mixing of the components, without use of external vacuum sources, external electric drives and external compressed air drives. With the prepacked mixing device it will be possible to produce polymethylmethacrylate bone cement purely by manual actuation, independently of additional external devices. Here, the manual actuation is to be simplified to the greatest possible extent. The opening of the monomer ampoule, or monomer ampoules, the monomer transfer, the generation of a vacuum or a negative pressure, and the mixing of the cement components is to be caused preferably by a simple movement, where possible, which has to be repeated particularly preferably only a few times, for example 3 to 5 times. The use of the vacuum mixing device for the user is thus to be simplified to the greatest possible extent, such that costly training can be limited or spared. Furthermore, operation of the vacuum mixing device simplified to the greatest possible extent is intended to minimize potential operating errors, thus increasing patient safety.

The polymethylmethacrylate bone cement powder can be combined and mixed with the monomer liquid within the vacuum mixing device by the medical user, without both cement components coming into contact with the medical user. Contact between the medical user and the polymethylmethacrylate bone cement powder and the monomer liquid must be ruled out. The vacuum mixing device to be developed is a full-prepacked vacuum mixing device. The vacuum mixing device is to be designed so that the monomer liquid is transferred into the polymethylmethacrylate bone cement powder by vacuum without the use of external vacuum pumps. Furthermore, the vacuum mixing device is to ensure the production of bone cement dough in a functional and reliable manner without external energy sources, such as compressed air, vacuum or electrical current, even under the simplest external conditions. The vacuum mixing device is also intended particularly preferably to do without an internal energy store, such as batteries or also mechanical energy stores, to the greatest possible extent. The vacuum mixing device is intended to be usable autonomously, without additional technical equipment.

Moreover, a device that is inexpensive to manufacture and that works reliably for the mixing of a medical cement and, if applicable, for storage of the starting components, and a method for the mixing of the bone cement is to be devised, in which the simplest possible manual operation can be used to mix the starting components, if possible without air inclusions arising in the mixing material.

The main component of the polymethylmethacrylate bone cement, as mixing material, shall be a powder and the second component shall be present in the form of a liquid. Preferably, it shall be possible to store the two starting components of the bone cement separately from each other in the vacuum mixing device and to combine them safely through the use of the device.

The objects of the invention are achieved by a vacuum mixing device for the mixing of polymethylmethacrylate bone cement from a monomer liquid and a cement powder, the vacuum mixing device comprising at least one cartridge comprising an evacuable interior for mixing of the bone cement, a mixing device for mixing the content in the interior of the at least one cartridge, which mixing device is arranged movably in the interior, a receptacle for receiving a separate container containing the monomer liquid or comprising an integrated container containing the monomer liquid, an opening device, which is arranged in the region of the receptacle in a manner movable relative to the receptacle so that, by moving the opening device, a separate container arranged in the receptacle is openable by means of the opening device, or the opening device is arranged in the region of the integrated container in a manner movable relative to the integrated container so that, by moving the opening device, the integrated container is openable by means of the opening device, a pump, in which a movable plunger for generating a negative pressure is arranged and delimits a pump chamber of the pump, and a connection line, which connects the interior of the at least one cartridge to the pump chamber of the pump, wherein the vacuum mixing device comprises an operating element that is operatable from outside, wherein the plunger in the pump is movable manually by means of the operating element, and wherein the opening device is movable relative to the receptacle or relative to the integrated container by means of the same operating element, and the mixing device in the interior of the cartridge is movable by means of the same operating element in order to mix the content in the interior of the cartridge.

The vacuum mixing device is preferably also suitable for storing the starting components of the polymethylmethacrylate bone cement. The monomer liquid and/or the cement powder are particularly preferably contained in the vacuum mixing device. The starting components of the polymethylmethacrylate bone cement are the cement powder and the monomer liquid, wherein the monomer liquid is preferably contained in a glass ampoule, which is arranged as a separate container in the receptacle. However, the monomer liquid can also be contained in a film bag as separate container or can be contained in the integrated container, which is formed by the receptacle or the vacuum mixing device itself.

The term "vacuum mixing device" is not to be understood incorrectly in the sense that a vacuum is mixed with something, but instead in the sense that the starting components of the bone cement, i.e. the monomer liquid and the cement powder, are mixable under vacuum or under a pressure lower than ambient pressure (negative pressure).

The term negative pressure always relates in the present case to a pressure relative to the surrounding atmosphere, which pressure is therefore lower than the surrounding atmospheric pressure.

On account of the specific requirements, such as the small volume of the interior of the cartridge, there is no need for more elaborate pump systems.

Provision can be made preferably so that the pump is integrated in the vacuum mixing device. Provision can also be made preferably so that the pressure in the interior of the at least one cartridge can be reduced by at least 50%, preferably can be reduced by at least 90%, by means of the pumping process.

Provision can also be made in accordance with the invention preferably so that the cement powder is contained in the interior of the cartridge. The cement powder then does not have to be filled into the interior of the cartridge.

By coupling the opening device to the operating element, the container in the receptacle or the integrated container is openable by means of the opening device by manually operating the operating element.

In the context of the present invention, the term "evacuable" means that a gas can be removed, i.e. for example a gas can be suctioned from the interior of the cartridge so that a negative pressure then remains in the interior of the cartridge. This negative pressure can be used in order to suck in the monomer liquid.

The vacuum mixing device comprises either a receptacle into which a separate container, such as a glass ampoule or a film bag, which contains the monomer liquid can be inserted, or an integrated container which is formed as an integral part of the vacuum mixing device and in which the monomer liquid is already contained.

Provision can also be made so that more than one cartridge is provided, each of which has an interior, wherein a mixing device is then provided in each interior and each interior is connected to the pump chamber of the pump or to a corresponding pump chamber of a plurality of separate pumps via a connection line.

The receptacle is also preferably suitable and intended for fixing a glass ampoule or the glass ampoule in the receptacle. The glass ampoule for this purpose clearly must be shaped appropriately. By way of example, the glass ampoule can be plugged into the receptacle by means of a press fit.

Provision can be made in accordance with the invention so that the receptacle is closed on one side by means of a lid.

Here, at least one gas-permeable opening can preferably be provided in the lid, through which opening gas can flow into the receptacle or can flow in once the monomer liquid is removed from the receptacle. This is intended to avoid the formation of a negative pressure in the receptacle, which negative pressure counteracts the flow of the monomer liquid into the interior of the cartridge.

The cartridge preferably has a pressure-tight feedthrough, through which a bar, a cable or a mixing shaft is passed, by means of which the mixing device is movable from outside the cartridge. For this purpose, the bar, the cable, or the mixing shaft is preferably mounted in the feedthrough rotatably and displaceably in the longitudinal direction. The content in the cartridge can be well mixed by means of the mixing device.

Preferred embodiments can be characterised in that the vacuum mixing device has a total weight less than 10 kg, particularly preferably has a total weight less than 2 kg, particularly preferably less than 1 kg.

These low weights are possible with the structure according to the invention of the vacuum mixing device with manually operable operating element and the pump. The low weight has the advantage that the vacuum mixing device is portable and transportable and usable without connection to supply lines and without great preparation efforts.

Provision can be made in accordance with the invention so that a sieve and/or a filter are/is arranged below the receptacle, the separate container, or below the integrated container so that the content in the opened integrated container or separate container flows through the sieve and/or the filter.

Glass splinters, film snippets, or other residues of the closure or of the separate or integrated container created when the separate or integrated container is opened by means of the opening device can thus be held back. A clogging of the fluid connection to the interior of the cartridge and a contamination of the bone cement to be produced is thus prevented.

Vacuum mixing devices according to the invention are characterised in that they do without an electric drive. Provision can thus be made in accordance with the invention so that the vacuum mixing device does not have an electric drive or at least the pump, the opening device and the mixing device are not driven by means of an electric drive. Instead, these component parts are driven in accordance with the invention via the manually operable operating element. Vacuum mixing devices according to the invention can also be constructed without electronics or electronic component parts. A vacuum mixing device according to the invention can thus also be characterised in that no electronics are installed therein or no electronics or electronic component parts are used at least in order to drive the pump, the opening device, and the mixing device. Electric motors or compressors therefore are not required in order to construct vacuum mixing devices according to the invention.

Furthermore, provision can be made in accordance with the invention so that the vacuum mixing device does not have any energy stores, in particular no electrical energy stores, such as a primary battery or a rechargeable battery, and no compressed gas store, such as a $CO_2$ compressed gas cartridge, or so that at least no energy stores, preferably no electrical energy stores or compressed gas stores, are used in order to drive the pump, the opening device, and the mixing device. The vacuum mixing device, however, preferably also does not have any resilient energy stores, such as tensioned springs.

In the case of vacuum mixing devices according to the invention, provision can be made so that the operating element is connected or connectable to the plunger in such a way that the plunger is movable manually in the pump by operation of the operating element.

As a result of this, the plunger is movable, in particular directly, by means of the operating element. Here, provision can be made so that the plunger is connected to the operating element only after a first operation of the operating element, in such a way that the plunger in the pump is moved by a further operation of the operating element. Here, a lever is particularly well suited for the embodiment of the operating element, which lever can be pulled or pushed or pivoted back and forth about an axis so that the separate container in the receptacle or the integrated container is opened after a first movement of the lever and in so doing the plunger and/or the mixing device are/is connected to the operating element in such a way that the plunger in the pump and/or the mixing device in the interior of the cartridge are/is moved in the event of a reverse movement of the lever. In addition, large forces can be transferred manually into the vacuum mixing device without difficulty by means of a lever.

Furthermore, provision can be made so that the receptacle, at least in regions, has closed side walls for receiving a glass ampoule as separate container, wherein the receptacle has at least one deformable closed side wall and a supporting element is provided opposite the deformable side wall, wherein the opening device is pressable via the operating element against the deformable side wall of the receptacle so that the deformable side wall deforms in such a way that a matching glass ampoule arranged in the receptacle can be broken open by means of the opening device.

As a result of this measure, the receptacle can be largely closed outwardly. In addition, it can be ensured as a result that a glass ampoule can also be opened within the closed receptacle without further monomer liquid being able to escape from the vacuum mixing device, whereby the risk of contamination of the surroundings of the vacuum mixing device with the content in the cartridge, in particular with the monomer liquid, can be ruled out or the risk of this is at least significantly reduced.

With a development of the present invention it is proposed for the opening device to have a first lever which is mounted rotatably about a first axis in relation to the receptacle or the integrated container, wherein a free end of the first lever is pushable against a deformable side wall of the receptacle or the integrated container, wherein the operating element is formed by a second lever which is mounted pivotably about a second axis in relation to receptacle or the integrated container, wherein the second axis divides the second lever into a short lever arm and a long lever arm, wherein an end of the short lever arm is to be pushed by manual operation of the long lever arm against the first lever so that the free end of the first lever pushes against the deformable side wall and deforms this in such a way that a separate container disposed in the receptacle is openable, or pushes the free end of the first lever against the integrated container so that the integrated container opens towards a fluid connection.

Here, provision can be made so that the separate container is a glass ampoule which matches the receptacle and which can be broken open by the pressure of the free end of the first lever or is a film bag which is arranged in the receptacle and which can be pierced or slit open or torn open by the pressure of the free end of the first lever.

Provision can also be made in such embodiments so that an edge is arranged at the free end of the first lever on the side facing towards the receptacle. The length ratio of the long lever arm to the short lever arm is preferably at least 5 to 1. Furthermore, provision can be made so that the second lever is to be rotated in the same plane as the first lever, wherein the movement of the second lever engages in the movement of the first lever. Provision can also be made preferably so that the second axis of the second lever is arranged above the first axis of the first lever, wherein the first axis of the first lever and the second axis of the second lever are preferably arranged parallel to one another.

With vacuum mixing devices of this type with glass ampoule, it is possible to break open a glass ampoule over a large area within the device or the cementing device, such that the monomer liquid flows out from the glass ampoule within a short period of time and is made available for mixing with the medical bone cement powder. With the aid of the two levers, which interact with one another, it is possible to direct the pressure on the glass ampoule in the direction in which the glass ampoule sits in the receptacle so that the glass ampoule cannot escape from the receptacle. At the same time, a very accurately defined local pressure can be exerted onto the glass ampoule, by means of which the glass ampoule in the vacuum mixing device can be broken open. With the aid of the deformable side wall, is possible to ensure that the force is transferred through this side wall into the interior of the receptacle and onto the glass ampoule, wherein the receptacle remains closed. An escape of the monomer liquid from the receptacle can thus be ruled out. With the aid of the sieve and/or the filter, glass splinters possibly created as the glass ampoule is opened can be held back. The monomer liquid can then be used for mixing with the bone cement powder.

The particular advantage of the device according to the invention also lies in the fact that any glass ampoules, regardless of the ampoule length and the geometry of the ampoule head, can be safely opened when the ampoule diameter is equal to or slightly greater than the inner diameter of the ampoule holder or the receptacle. It is also a particular advantage that when breaking the ampoule wall in the region of the ampoule base, the liquid contained in the glass ampoule immediately flows out completely, independently of the surface tension. By contrast, in the case of conventional ampoule breakers, the liquid flows out through the relatively narrow cross-section of the ampoule neck, after separation of the ampoule head, significantly more slowly. Here, reasonably high outflow speeds are attained only when the cross-section of the ampoule neck is large enough so that the surface tension of the liquid cannot hold the meniscus of the liquid in the ampoule neck.

The receptacle is preferably a hollow cylinder. The receptacle likewise preferably consists of an elastomer or comprises an insert made of an elastomer, such as an ethylene propylene diene (EPDM) rubber.

Provision can also be made here so that a shoulder for supporting the glass ampoule is arranged in the receptacle, wherein the shoulder is smaller than half the area of the ampoule base or the ampoule cross-section. Here, provision can in turn be made preferably so that the shoulder is arranged in the receptacle in such a way that the distance between the shoulder and a sieve and/or filter arranged there below is the same size as or greater than the outer diameter of the glass ampoule to be inserted.

With a vacuum mixing device that can be provided particularly easily and economically, it is proposed for the operating element to be manually movable, preferably to be a lever pivotable about an axis, wherein the operating element is operatively connected to or is to be brought into operative connection with the opening device, the pump, and the mixing device in such a way that with a first operation of the operating element a separate container in the receptacle or the integrated container is to be opened, and with a further operation of the operating element the plunger in the pump is to be driven, and the mixing device in the interior is to be driven.

A force which is to be applied manually and which acts on the operating element, in particular the lever, can hereby be used in order to firstly open the separate or integrated container and then drive or move the pump and the mixing device by means of the same operating element. Levers as operating elements are particularly well suited for transferring manual force into the vacuum mixing device. This is also the case because it is possible to increase the usable force via the length of the lever arm.

Here, provision can be made so that the plunger of the pump, and/or the mixing device are/is to be driven via a flexible cable and/or a rod, wherein a detent means is provided on the flexible cable and/or the rod and after first-time operation of the operating element engages with a mating detent means on the operating element or with a mating detent means connected to the operating element so that, with operation of the operating element subsequent to the latching, the plunger of the pump and/or the mixing device are/is to be driven via the cable and/or the rod by means of the operating element.

The force can thus be transferred from the operating element to the plunger and/or the mixing device. The flexible cables are particularly well suited for the transfer of force, since the direction of the force can be deflected therewith without complex mechanics. The flexible cable is preferably sufficiently stiff or rigid so that the plunger and/or particularly the mixing device can be moved back and forth in both directions. The cable can be guided and/or supported for this purpose. By way of example, the cable for this purpose can be guided in a channel, or can be supported and/or deflected at suitable points by a housing and by struts and/or deflection rollers in the housing. Due to the use of the detent means and the mating detent means, it is possible to ensure that the separate container in the receptacle or the integrated container is firstly opened and the monomer liquid runs out completely, before the pump or the plunger of the pump and/or the mixing device is operated. By way of example, it is thus possible to prevent the pump from being operated before the monomer liquid is available.

Is also proposed for the mixing device to be axially movable in the interior in the longitudinal direction by operation of the operating element.

A very comprehensive mixing of the interior is hereby achieved in particular for a cylindrical interior. At the same time, the mixing device can be constructed in a compact manner, since it does not have to extend along the entire length of the interior.

Provision can also be made preferably so that the mixing device is rotatable about the longitudinal axis of the interior by operation of the operating element in the interior, wherein preferably for this purpose a cylinder connected to the mixing device and having an external thread moves in a stationary sleeve having a matching internal thread so that, when the cylinder moves along the longitudinal direction within the sleeve, a rotation of the cylinder is enforced, wherein the rotation of the cylinder transfers to the mixing device in the interior of the cartridge.

An even more thorough mixing of the content in the interior is achieved hereby. Bone cement clinging to the wall of the interior can also be effectively mixed as a result. The bone cement is thus mixed more quickly and more effectively.

With a development of the present invention provision can also be made so that the pump chamber of the pump is gas-tight and is arranged in the interior of the pump, wherein the plunger is manually drivable via the operating element in at least one direction, such that the pump chamber is to be enlarged by the movement of the plunger and the interior of the at least one cartridge is to be evacuable through the connection line by means of the resultant negative pressure created in the pump chamber.

A particularly good pumping effect of the pump is hereby achieved, and therefore the vacuum that can be generated in the interior of the cartridge is improved. The plunger with the operating element can particularly preferably be moved manually repeatedly in two directions along the axis of the pump chamber so that a repeated pumping in order to evacuate the interior of the cartridge is possible.

Here, provision can be made so that the volume increase of the pump chamber is at least as large as the free volume of the interior of the cartridge, and the volume increase of the pump chamber is preferably at least as large as the sum of the volume of the interior of the cartridge in which the cement powder of the PMMA bone cement is contained, and the volume of the connection line, and the volume of a fluid connection between the interior of the cartridge and the receptacle for the separate container or the integrated container, and the volume of a monomer liquid to be mixed with the cement powder of the PMMA bone cement in the cartridge.

It is thus ensured that the pump can evacuate the interior of the cartridge with just one stroke or with few strokes of the plunger. Here, the volume of the pump chamber prior to the pumping process is ideally as small as possible. Provision can thus be made preferably so that the volume of the pump chamber after the pumping process is at least 10 times greater than the volume of the pump chamber prior to the pumping process, particularly preferably is at least 20 times greater than the volume of the pump chamber prior to the pumping process. The plunger preferably does not bear tightly in an areally flush manner against the interior of the pump, in particular the top surface of a hollow cylinder comprising the connector for the connection line, such that the plunger area is not fixedly sucked against this area such that it can only be moved with difficulty in order to start the movement. For this purpose, spacers can be provided on the top surface in the pump chamber and/or on the plunger in the pump chamber.

In order to be able to operate the pump with a number of actuations of the actuating element, or so as to be able to utilise a multiple stroke of the plunger of the pump, provision can be made so that a first one-way valve is arranged in the connection from the pump chamber to the connection line or in the connection line, which first one-way valve is open or is actively opened when a pressure lower than in the interior of the cartridge prevails in the pump chamber and is in a closed state or is actively closed when a pressure equal to or higher than in the interior of the cartridge prevails in the pump chamber, and a second one-way valve preferably connects the pump chamber to the surroundings of the pump, which second one-way valve is open or is actively opened when a pressure higher than in the surroundings of the pump prevails in the pump chamber and is in the closed state or is actively closed when a pressure equal to or lower than in the surroundings of the pump prevails in the pump chamber, wherein the one-way valves are preferably check valves.

With the first one-way valve, a flow is possible from the interior of the cartridge into the pump chamber, but flows in the opposite direction are largely prevented. As a result of the second one-way valve, an overpressure in the pump chamber can be relieved via the second one-way valve.

A particularly good vacuum or a particularly good negative pressure in the interior of the cartridge can be generated hereby with repeated pumping by multiple movement of the plunger and can be maintained or improved further during the mixing process as well.

Furthermore, provision can be made so that the plunger is mounted axially movably in a hollow cylinder, wherein the hollow cylinder is closed on a first side or is closed apart from a feedthrough for a rod or cable connected to the operating element and the plunger, in particular is closed by a closure, wherein a pump chamber is preferably formed in the hollow cylinder between the plunger and the first closed side, wherein the hollow cylinder is particularly preferably open on a second side.

The pump chamber and the plunger preferably have a cylindrical geometry. As a result of these measures and also as a result of the cylindrical geometry, a combined pump that is particularly easily and inexpensively manufactured is proposed, which is easily operated and is particularly unsusceptible to malfunctions.

It is also proposed that the plunger is connected or connectable to the operating element via a rod and/or a cable, and preferably for the plunger to be moved in the pump by operation of the operating element.

A particularly simple vacuum mixing device is hereby provided, with which there is no risk of possible interruptions. The direct connection of the operating element to the plunger via the cable and/or the rod can be provided with a one-part injection-moulded part made of plastics material. Alternatively, a transmission or a gearing can also be provided, by means of which the force exerted onto the operating element is transmitted to the plunger in order to enable a more powerful movement of the plunger.

In a further development of the vacuum mixing device, provision can be made so that a movable dispensing plunger for dispensing the mixed bone cement from the cartridge is arranged in the interior of the cartridge, wherein the dispensing plunger is preferably releasably locked or lockable in order to prevent a movement of the dispensing plunger under the action of the negative pressure.

The operation of the vacuum mixing device is simplified by the dispensing plunger.

Here, provision can be made so that the dispensing plunger has a passage with a gas-permeable pore plate, which is impermeable for cement powder, wherein the passage with the pore plate connects the interior of the cartridge to the connection line and/or the surroundings in a gas-permeable manner, wherein the passage is closable in a gas-tight manner, preferably is closable in a gas-tight manner by means of a sealing plunger of the dispensing plunger.

With the pore plate it is possible to ensure that the interior of the cartridge with the cement powder therein can be sterilised with the aid of a gas, such as ethylene oxide, without there being any risk that the cement powder will pass from the interior of the cartridge externally into the surroundings.

Provision can also be made preferably so that the cartridge is a cement cartridge filled with cement powder and a separate container containing a monomer liquid is arranged in the receptacle or a monomer liquid is contained in the integrated container, wherein the receptacle or the integrated container is preferably connected in a liquid-impermeable manner to the interior of the cement cartridge and/or the interior of the cement cartridge is connected or connectable in a gas-permeable manner to the pump.

The monomer liquid can thus be transferred from the separate or integrated container into the interior of the cartridge by means of the same pumping movement or the same pumping process by means of which the interior of the cartridge is evacuated. The vacuum or the negative pressure generated manually by the pump is used here at the same time to suck the monomer liquid into the cartridge. In particular, the separating element to be opened is openable in accordance with the invention by means of the operating element, preferably once the integrated container or the separate container has been opened.

Provision can also be made so that the cartridge, the pump, and all lines and also the receptacle or the integrated container are fixedly and/or releasably connected to a common base part and/or a housing, wherein the pump and all lines as well as the receptacle or the separate container are preferably fixedly connected to the base part and/or the housing, and the cartridge is releasably connected to the base part and/or the housing.

A vacuum mixing device of this type can be easily placed and can be easily operated. The use of the vacuum mixing device is thus simplified. Merely a flat substrate for setting up the vacuum mixing device must be provided at the site of use, which in most OP areas does not pose any problems.

In accordance with one embodiment provision can be made so that the separate container containing the monomer liquid is a film bag which can be cut open or torn open in the receptacle by means of the opening device, or is a glass ampoule which can be broken open in the receptacle by means of the opening device.

Commercially available packaging options for the monomer liquid can thus be used, without having to open these outside the vacuum mixing device.

It is proposed for the receptacle or the integrated container to be connected or connectable via a fluid connection to the interior of the cartridge, wherein the mouth of the fluid connection into the interior of the cartridge is preferably arranged on the opposite side of the mouth of the connection line between the interior and the pump chamber.

As a result, the monomer liquid can be conveyed via a dedicated line (the fluid connection) into the interior of the cartridge.

Here, provision can be made so that a loop is arranged in the fluid connection, such that the monomer liquid running out from the opened separate container or the integrated container cannot flow into the interior of the cartridge without negative pressure in the interior of the cartridge, wherein a storage volume for receiving the liquid volume of the monomer liquid is preferably arranged below the receptacle or the integrated container.

With correct placement of the vacuum mixing device, it is thus possible to ensure that the monomer liquid cannot flow unintentionally into the cartridge without influence of the negative pressure and cannot cure there unintentionally. It is thus possible to prevent the monomer liquid from passing into the interior of the cartridge through the liquid line already when the separate or integrated container (for example the monomer glass ampoule) is opened. This loop, which for example can be constructed by a reversed U-shaped loop of the fluid connection, means that, before any movement of the plunger of the pump, the monomer liquid remains within the vacuum mixing device until at the height of the apex in the fluid connection, whereby a premature entry of the monomer liquid to the cement powder is prevented, wherein in particular in the case of highly viscous cements a premature contact of even small volumes of the monomer liquid with the cement powder can lead to a clogging of the fluid connection or a fluid connection formed as a nozzle, as described in U.S. Pat. No. 8,662,736 B2. The fluid connection can be transparent or translucent so that the user can visually monitor the monomer transfer. For this purpose, a viewing window can be provided in the vacuum mixing device, through which window the loop with the highest apex can be seen.

With a development of the present invention, it is also proposed for a negative pressure to be generated in the pump chamber as a result of the movement of the plunger in the pump, wherein a gas is evacuable through the connection line from the interior of the at least one cartridge by means of the negative pressure.

A particularly simple and unsusceptible design is hereby provided.

Provision can also be made in accordance with the invention so that the pump is constructed with a hollow cylinder, wherein the hollow cylinder is connected or connectable at the first and at the second hollow cylinder end to the interior of the cartridge, a gas-tight closure at one cylinder end, the plunger, which is arranged in the hollow cylinder in a gas-tight and axially movable manner, wherein the plunger in the pump is movable by means of the manually operable operating element, wherein, with a movement of the plunger by means of the manually operable operating element, the plunger is movable axially oppositely to the closure and gas can thus be evacuated from the interior of the cartridge, wherein the operating element is operatively connected to the opening device, and wherein the operating element is connected to the mixing device in the interior of the cartridge in such a way that the mixing device in the interior of the cartridge is movable with operation of the operating element.

This design is particularly simple, and the parts essential for it can be manufactured from plastics material by injection moulding.

With a particularly preferred embodiment of the present invention, provision can be made so that the pump, the opening device, and the mixing device are drivable via the movement of the operating element, wherein the operating element is preferably moved by the action of manual force.

The vacuum mixing device therefore does not require any energy stores or any electric or electronic drives. This is desirable since the vacuum mixing device is intended for one-time use and in this way can be recycled more easily. In addition, the vacuum mixing device is ready for use in principle, and does not require any connections, such as cables or compressed gas tubes, in order to be used.

The objects forming the basis of the present invention are also achieved by a method for mixing polymethylmethacrylate bone cement in an interior of a cartridge of a vacuum mixing device, in particular a vacuum mixing device of the type described above, in which method an operating element is operated and an integrated container of the vacuum mixing device or a separate container, which is arranged in a receptacle of the vacuum mixing device, is thus opened, wherein a monomer liquid contained in the integrated container or the separate container then runs out as first component of the bone cement, by means of a subsequent, further operation of the operating element, a movement of a plunger of a pump of the vacuum mixing device is driven, wherein a negative pressure is generated in a pump chamber of the pump by means of the movement of the plunger, wherein the interior of the cartridge is evacuated by means of the pump driven in this way and the monomer liquid is conducted into the interior of the cartridge by means of the negative pressure in the interior of the cartridge, wherein a bone cement powder as second component of the bone cement is already disposed in the interior of the cartridge, and a mixing device in the interior of the cartridge is moved as a result of the operation of the operating element and a bone cement dough in the interior of the cartridge formed from cement powder and the monomer liquid is mixed as a result of the movement of the mixing device.

Here, provision can be made so that the volume of a pump chamber of the pump is increased by the manual movement of the plunger and the interior of the cartridge is evacuated due to the negative pressure created as a result.

The pump can thus be provided in a simple way.

Provision can also be made in accordance with the invention so that a cement powder is contained in the interior of the cartridge and a gas is evacuated from the interior of the cartridge by means of the pump, a monomer liquid is introduced into the interior of the cartridge, and the monomer liquid is mixed with the cement powder in the evacuated interior of the cartridge due to a movement of the mixing device.

A design that can be provided particularly easily and reliably can be achieved as a result of the specified combination and interaction of the method steps.

Furthermore, provision can be made so that the plunger of the pump is moved by means of the operating element, whereby a negative pressure relative to the surrounding atmosphere is generated in the pump, in so doing gas from the interior of the cartridge is sucked into the pump chamber of the pump through a connection line, and the pump plunger of the pump is moved by means of the operating element, whereby a pressure is exerted onto the monomer liquid in the pump chamber, the monomer liquid is pushed through a fluid connection from the pump chamber into the interior of the cartridge, the vacuum mixing device in the interior of the cartridge is then moved by operation of the same operating element, and in so doing the cement powder is mixed with the monomer liquid, the cartridge containing the mixed cement dough is removed, and the cement dough is pressed out from the cartridge by means of an axial movement of a dispensing plunger.

The method is hereby enhanced such that, at the end, a cement cartridge containing a bone cement dough mixed under vacuum is provided and can be used immediately.

Lastly, provision can also be made so that the cement powder is arranged in the cartridge, the monomer liquid is arranged in a receptacle separate from the cartridge, wherein the monomer liquid is contained in an integrated container or in a separate container, preferably in a glass ampoule in the receptacle, the integrated container or the separate container is opened by operation of the operating element and a resultant movement of the opening device, before the plunger is driven by a further operation of the operating element, the plunger is then moved axially in a hollow cylinder, whereby a negative pressure compared to the surrounding atmosphere is generated, in so doing gas from the interior of the cartridge is sucked through the connection line into the hollow cylinder, and monomer liquid is sucked into the cartridge by means of the negative pressure formed in the interior of the cartridge.

The method is thus further enhanced.

Methods according to the invention can also be characterised by the intended application or use of component parts of vacuum mixing devices according to the invention.

The invention is based on the surprising finding that it is possible with a single operating element to operate or drive the pump and the mixing device and also to operate the opening device. This has the advantage that there is no need for any complicated handling instructions for the operating individual. All sequences can be controlled and driven by operation of the sole operating element. The vacuum mixing device is thus simplified to the greatest possible extent. At the same time, there is no need for any energy stores for the drive, and there is no need for any electrical or electronic control unit in order to drive and control the pump, the mixing device and the opening device.

At the same time, it is possible with the aid of the pump, which is to be driven manually, to provide a vacuum mixing device that is independent of internal and external power sources and other supply lines. The vacuum mixing device according to the invention can be constructed in a compact, simple and space-saving manner. The pump, the opening device, and the entire vacuum mixing device can be constructed using the simplest means, such that the entire vacuum mixing device can be used as a disposable system. The pump can also be used and in accordance with the invention preferably is also used to transfer a monomer liquid into the cement powder. The two components of the PMMA bone cement can then be mixed in the vacuum or in the negative pressure.

A device for generating a vacuum or for generating a negative pressure is contained in the cementing systems according to the present invention and is suitable for the temporary generation of a negative pressure before and during the mixing of a powdered component with a liquid monomer component of the polymethylmethacrylate bone cement.

The idea forming the basis of the invention is based on the finding that only a relatively small amount of energy and therefore a low manual application of force is necessary in order to open the container for the monomer liquid in order to generate the vacuum or the negative pressure in a cartridge, which is necessary in order to mix the starting components of a bone cement under the negative pressure or the vacuum, and in order to move the mixing device for mixing the bone cement dough in the interior of the cartridge. The amount of energy in order to transfer the monomer liquid into the cement powder is also small. This small amount of energy can be applied readily by operation of a lever as operating element. The vacuum mixing device hereby can be handled in a simple manner and is easily operated and is also independent of internal and external energy stores. Due to a suitable structure, the order of the sequences can also be controlled, specifically the monomer container is openable first and only then can the pump and the mixing device be driven.

The idea of the invention is also based on the fact that a negative pressure is generated in a hollow cylinder of the pump by manual actuation of an operating element with a plunger connected thereto in a hollow cylinder of the pump, wherein the negative pressure spreads via a line means into the cartridge and the monomer liquid is sucked from an opened monomer liquid container into the cartridge, in which cement powder is disposed. The cement components are then mixed manually with the aid of a mixing device, which is to be driven simultaneously via the same operating element.

By way of example, the invention can be implemented by means of the following method, in which the following functions are performed in the mixing device by activation with a manually operated lever or more generally a manually operated operating element:

$1^{st}$ step: actuation of the manual lever or operating element and breaking of the ampoule or ampoules, leakage of the monomer liquid within 1 to 2 seconds into a reservoir, which is connected to a line means and a nozzle, wherein the nozzle points via its opening into the interior of the cartridge; latching of a resilient rod into a mating detent means of the lever at the stop point of the lever, wherein the rod is forked into a first part and a second part;

$2^{nd}$ step: return movement of the manual lever or operating element into the starting position, wherein a plunger in a hollow cylinder is moved axially by the first part of the resilient rod and a negative pressure is created behind the plunger in the hollow cylinder; forwarding of the negative pressure via a check valve and a line means for vacuum connection into the interior of the cartridge; creation of a negative pressure in the interior of the cartridge; suctioning of the monomer liquid from the reservoir into the cartridge; movement of the second part of the resilient rod, which is rotatably connected to a first sleeve, which has at least one outermost lobe, which is arranged movably in a steep thread of a second sleeve, such that a resilient stirring bar (as mixing shaft) is fixedly connected to the first sleeve so that the first sleeve is rotated by engagement of the lobe in the steep thread in the event of an axial movement of the first sleeve through the (or in the) second sleeve, whereby the stirring bar rotates and moves axially in the cartridge;

$3^{rd}$ step: further actuation of the manual lever or operating element; movement of the first sleeve in the second sleeve; axial movement of the stirring bar in the cartridge with rotation about the longitudinal axis;

$4^{th}$ step: repetition of the $2^{nd}$ and $3^{rd}$ steps until the cement dough is homogeneously mixed;

$5^{th}$ step: release of the cartridge or cartridge system by unscrewing and removal of the mixing bar (of the mixing shaft) with the mixing element; and collapsing of the mixing elements (the mixing blades of the mixing device).

The key advantage of the invention is that a prepacked mixing system is proposed which can be used in the simplest manner possible, without specific training measures, by the medical user by means of simple manual actuation in order to produce a polymethylmethacrylate bone cement dough within a few seconds (for example within 40 seconds). It is also advantageous that use errors are minimised on account of the maximally simplified operation, thus resulting in an improvement in patient safety.

The vacuum mixing device according to the invention can be provided substantially inexpensively using simple plastics material parts to be produced by plastics material injection moulding. The particular advantage of the device according to the invention lies in the fact that the device can be operated without external aids, such as vacuum pumps and vacuum tubes driven by compressed air, and without energy sources, such as compressed air or batteries. The vacuum mixing device according to the invention can be used autonomously and can be used even under the simplest or most difficult operation conditions. A closed full-prepacked vacuum cementing system for price-sensitive markets is provided by means of the vacuum mixing device according to the invention.

BRIEF DESCRIPTION OF THE DRAWINGS

Further exemplary embodiments of the invention will be explained hereinafter on the basis of eight schematically illustrated Figures, without, however, intending to limit the invention hereto. In the Figures.

DETAILED DESCRIPTION OF THE DISCLOSURE

Figure 1:
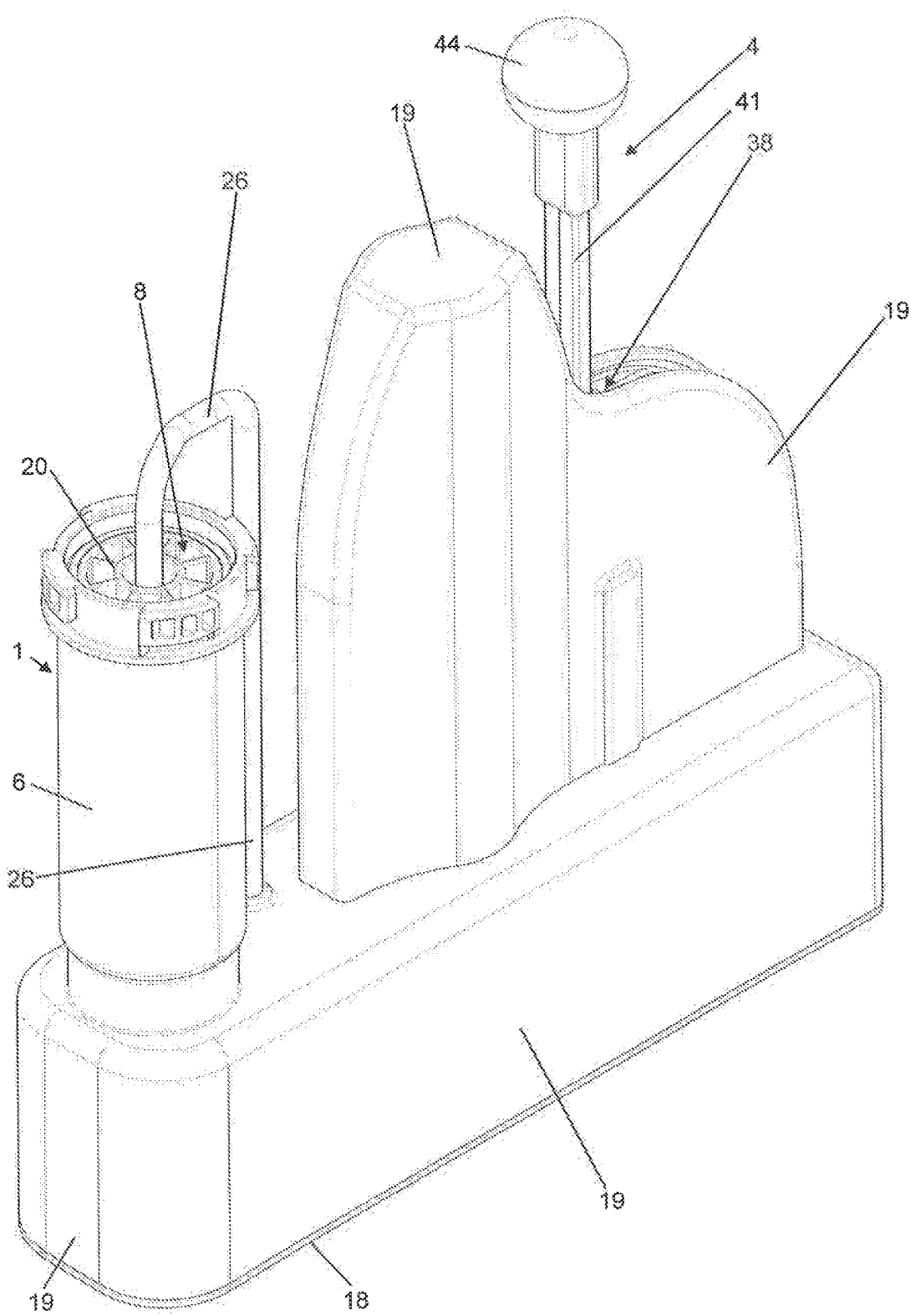
FIG. 1: shows a schematic perspective view of a vacuum mixing device according to the invention.

FIGS. 1 to 8 show various views of a vacuum mixing device according to the invention before and during operation. The vacuum mixing device consists fundamentally of five parts, specifically a cartridge system 1, a liquid container 2, a pump 3, which is to be driven manually, an operating element 4, and an opening device 5.

A central part of the cartridge system 1 is a cartridge 6 having a cylindrical interior which is closed at its upper side by a two-part dispensing plunger 8 which is arranged movably in a longitudinal direction in the cylindrical interior of the cartridge 6. The cartridge 6 thus has a cylindrical interior with circular base area. The cartridge 6 contains a cement powder 9 as starting component for a bone cement.

A mixing device 10 having two or more mixing blades 10 is also arranged in the interior of the cartridge 6, wherein the mixing device 10 is mounted rotatably and displaceably in the longitudinal direction in the interior of the cartridge 6 and is secured to a mixing shaft 12 or to a cable 12, which is guided rotatably and displaceably in the longitudinal direction through a feedthrough in the underside of the cartridge 6 into the interior of the cartridge 6. The feedthrough is pressure-tight and gas-tight for this purpose. The mixing shaft 12 can also be embodied as a flexible rod 12.

The cartridge system 1 is connected to the liquid container 2 and the pump 3 via a base part 18 and a housing 19. The liquid container 2, the pump 3, part of the operating element 4, and the opening device 5 are surrounded by the housing 19, wherein part of the operating element 4 protrudes from the housing 19, whereas the cartridge system 1 is screwed onto the housing 19. The cartridge 6 ends at its underside in a connection piece having an internal thread 14, which is screwed onto an external thread 16 on a connection piece of the housing 19. The base part 18 here forms the stand 18 of the compact vacuum mixing device. The cartridge 6 is thus releasable from the housing 19 and therefore the rest of the vacuum mixing device. When the bone cement 96 (see FIG. 8) is mixed to a finished state in the interior of the cartridge 6 by means of the vacuum mixing device, the cartridge 6 can thus be unscrewed from the housing 19, and a dispensing pipe (not shown) can be screwed into the internal thread 14, through which pipe the finished bone cement dough 96 (see FIG. 8) can be driven out by advancing the dispensing plunger 8 in the direction of the internal thread 14. A static mixer can be provided in the dispensing pipe, which mixer provides an additional mixing of the bone cement dough 96.

The two-part dispensing plunger 8 has a sealing plunger 20 and a sterilisation plunger 22. The sterilisation plunger 22 has a membrane or pore plate 24, which is permeable for a sterilising gas, but is not permeable for the cement powder 9. The sterilisation plunger 22 is inserted into the cartridge 6 once the cement powder 9 has been filled therein and closes the interior of the cartridge 6 with respect to the outside. The content in the cartridge 6 can then be sterilised with ethylene dioxide through the gas-permeable membrane or pore plate 24.

This sealing plunger 20 can be pushed into the sterilisation plunger 22 and can be connected thereto in a gas-tight and pressure-tight manner. The plunger parts 20, 22 secured to one another then together form the dispensing plunger 8, by means of which the content in the cartridge 6 can be pressed out through the opening in the connection piece having the internal thread 14. The sterilisation plunger 22 is initially locked on the side opposite the side with the opening in the connection piece having the internal thread 14 (at the top in FIGS. 3, 4 and 6 to 8), wherein the locking is releasable. As a result of the locking, the sterilisation plunger 22 is prevented from moving undesirably during the sterilisation of the interior of the cartridge 6 and also the cement powder 9.

The mixing blades 10 inside the cartridge 6, i.e. in the interior of the cartridge 6, are rotatable via the mixing shaft 12 or the cable 12 and are movable in the longitudinal direction of the cartridge 6.

Figure 5:
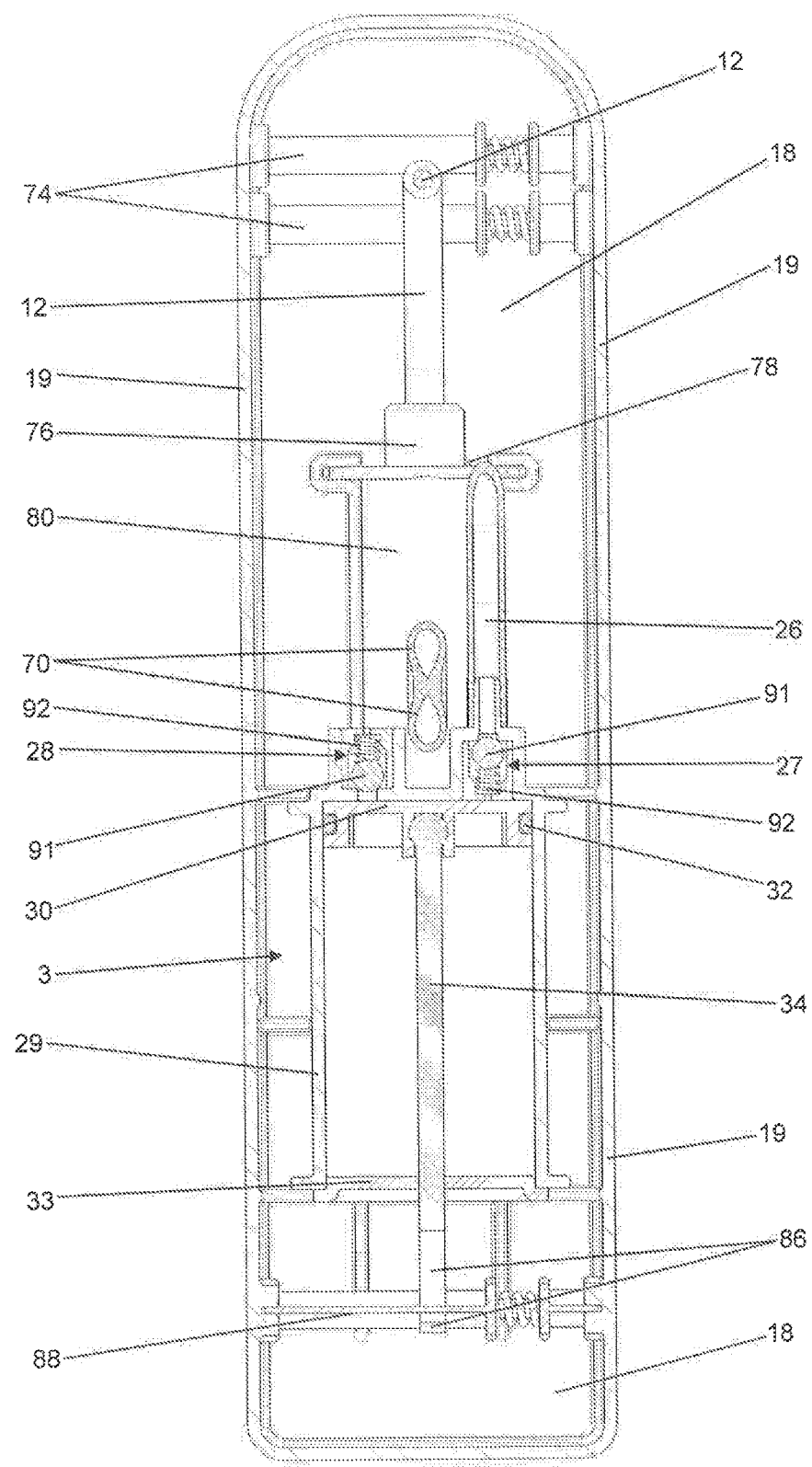
FIG. 5: shows a schematic cross-sectional view of the vacuum mixing device according to FIGS. 1 to 4 with a plane of section perpendicular to the section of FIGS. 3 and 4.
Figure 6:
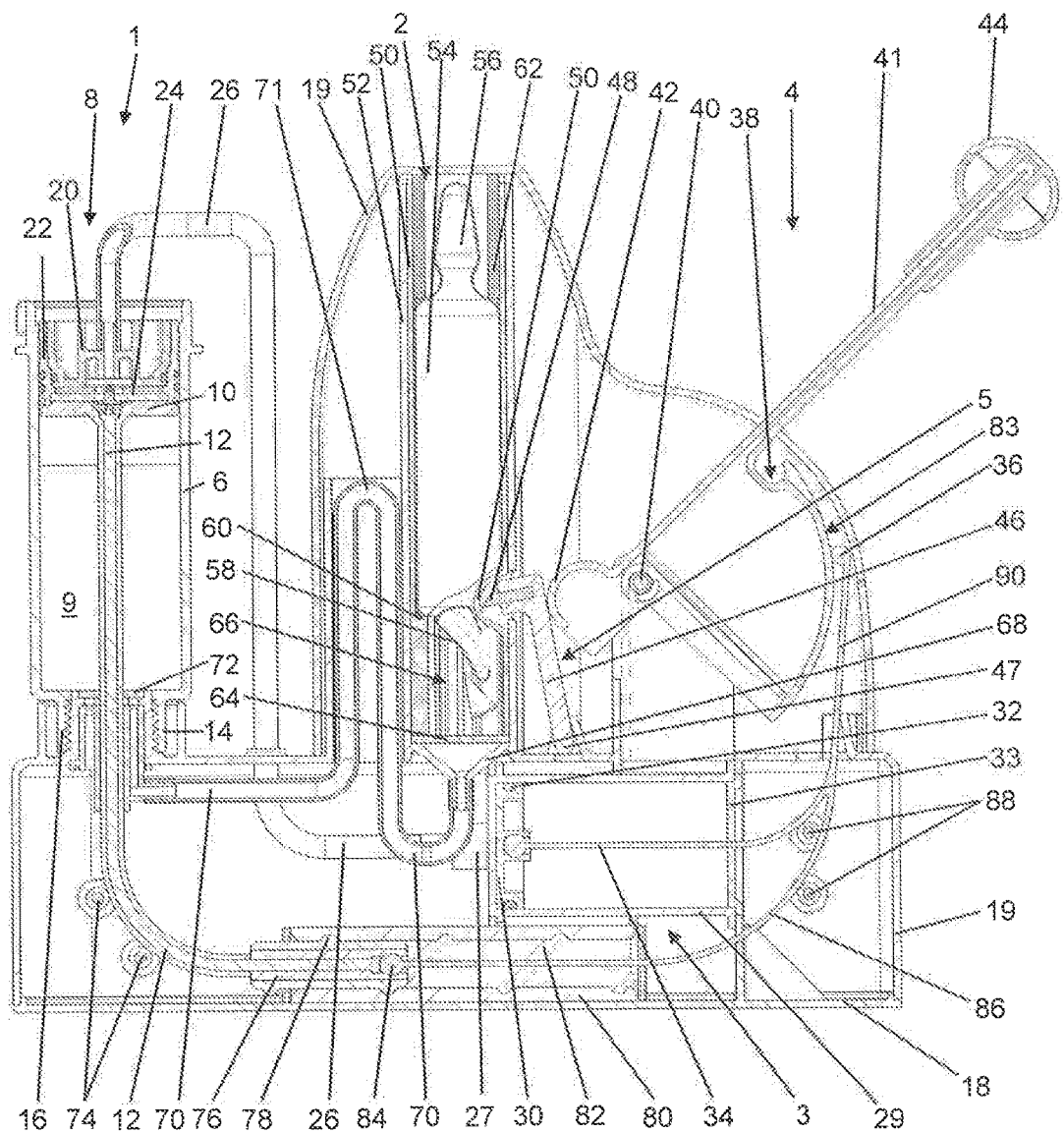
FIG. 6: shows a schematic cross-sectional view of the vacuum mixing device according to FIGS. 1 to 5 during the operation with broken-open glass ampoule.

A feedthrough is provided in the sealing plunger 20, which feedthrough is connected to a connection line 26 in the form of a flexible vacuum line 26. This sealing plunger 20 is otherwise closed in a pressure-tight manner with the cartridge 6. The vacuum line 26 opens via a first check valve 27 into the pump 3, such that only a flow in the direction into the pump 3 is possible. The pump 3 is additionally connected to the surroundings via a second check valve 28, such that an overpressure created in the pump 3 can be discharged via the second check valve 28. Details regarding the check valves 27, 28 are illustrated in FIG. 5 and will be described further below in the description. A filter (not shown) can be provided optionally at the second check valve 28, by means of which filter methacrylate vapours or other disruptive chemical substances can be filtered out from the gas flowing out.

The pump 3 has a stable hollow cylinder 29. The hollow cylinder 29 is separated in a pressure-tight manner into two parts via a plunger 30. For this purpose, the plunger 30 has a peripheral seal 32, which terminates with the inner wall of the hollow cylinder 29. The plunger 30 is connected to a cable 34 or a flexible rod 34 made of a stable resilient plastics material or made of a metal, such as steel, which leads through a feedthrough in a rear-side closure 33. On the front side, the pump 3 is closed by a front-side closure, in which there are disposed the connections for the check valves 27, 28. The closure 33 is connected on the sides of the hollow cylinder 29 opposite the check valves 27, 28. The vacuum line 26 is guided as far as the pump 3, such that the feedthrough in the sealing plunger 20 is connected in a pressure-tight manner via the vacuum line 26 to the pump 3, more specifically to a pump chamber 94 (see FIG. 8) of the pump 3. The pump chamber 94 is delimited by the inner walls of the hollow cylinder 29, by the front-side closure, and by the plunger 30.

Figure 7:
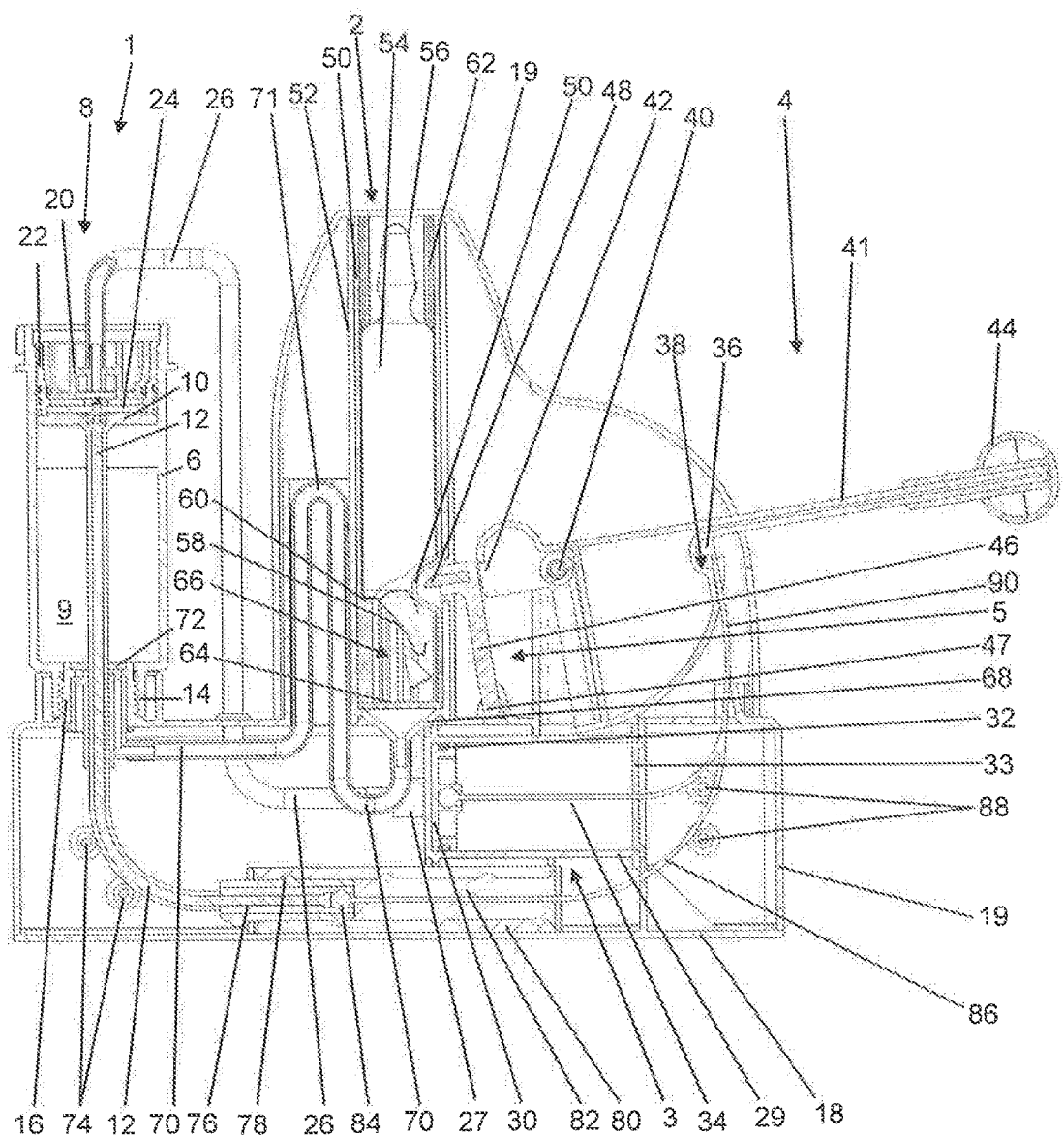
FIG. 7: shows a schematic cross-sectional view of the vacuum mixing device according to FIGS. 1 to 6 during the operation with latched cable or latched rod.
Figure 8:
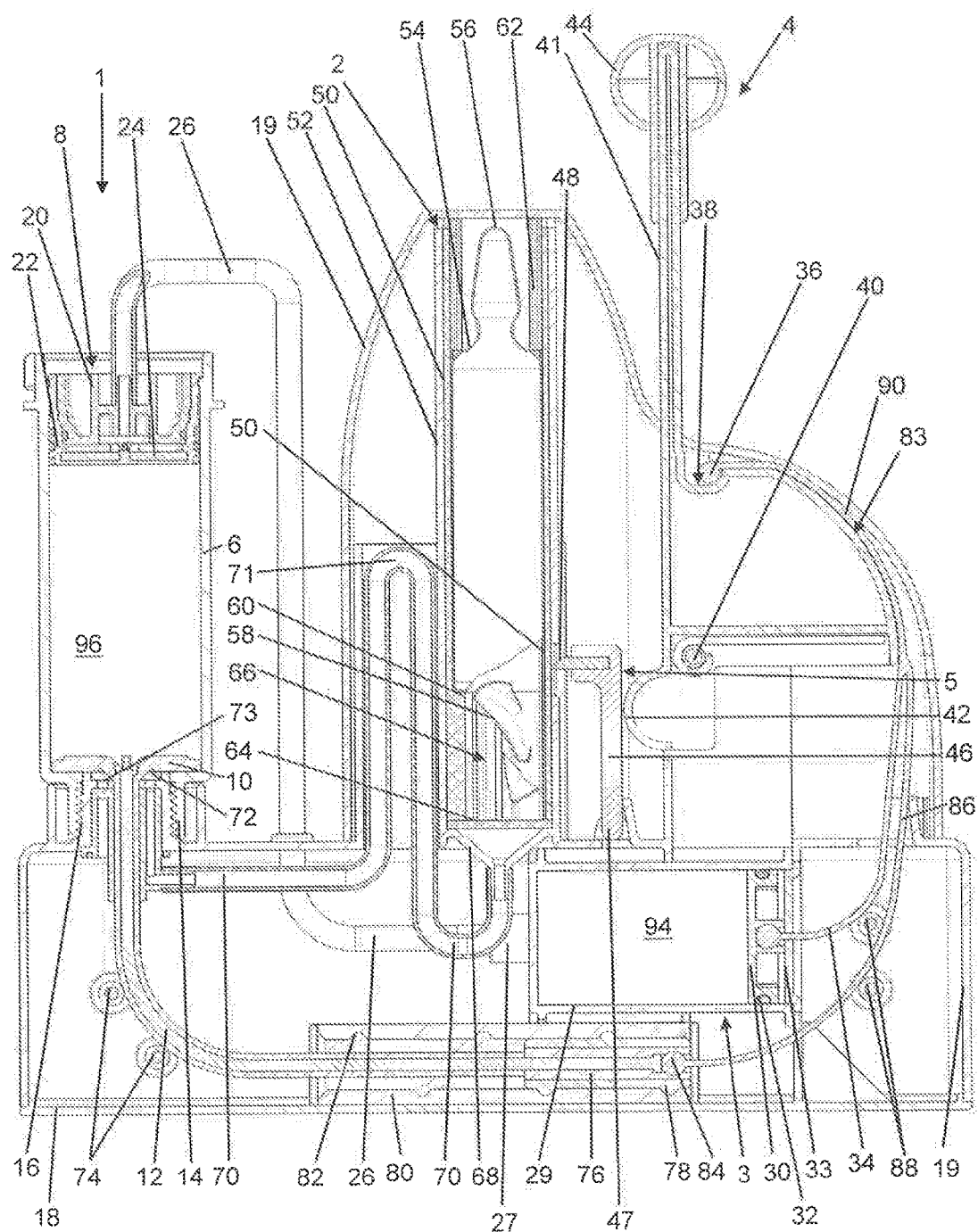
FIG. 8: shows a schematic cross-sectional view of the vacuum mixing device according to FIGS. 1 to 7 during the operation at the time of pumping and mixing.

The cable 34 is connected to a detent means 36, which can latch with a mating detent means 38 (see FIGS. 7 and 8). The mating detent means 38 is part of the operating element 4, which is constructed as a lever 4 which can be rotated or pivoted about an axis 40. The lever 4 comprises two lever arms 41, 42, which extend from the axis 40 in different directions. The actual operating part of the lever 4 is formed by the first lever arm 41, which ends in a handle 44, which can be manually operated from outside. The first lever arm 41 thus protrudes out from the housing 19, and the handle 44 is arranged outside the housing 19 and can be manually operated by the user of the vacuum mixing device. Here, a considerable force can be transferred into the interior of the vacuum mixing device via the first lever arm 41 and is sufficient and is used in accordance with the invention to drive the opening device 5, the pump 3, and the mixing device 10.

The second lever arm 42, as the lever 4 is pivoted or as the lever 4 is pushed down, pushes against the opening device 5 and drives this. For this purpose, the opening device 5 is constructed with a lever 46, which is mounted so as to be rotatable or pivotable about an axis 47. At the end of the lever 46 opposite the axis 47, an insert having an edge 48 is provided, which bears against the receptacle 2 or the liquid container 2.

The liquid container 2 or the receptacle 2 comprises an inner resilient insert 50, which for example can consist of a rubber, and a rigid hollow cylinder 52 made of a plastics material, such as plastic. A glass ampoule 54 containing a monomer liquid is inserted into the receptacle 2 or the liquid container 2. The monomer liquid forms a bone cement dough 96 together with the cement powder 9 from the cartridge 6 when these are mixed together. The inner walls of the resilient insert 50 bear against the glass ampoule 54. The glass ampoule 54 has an ampoule head 56 and an ampoule base 58 opposite the ampoule head 56. The glass ampoule 54 sits via the ampoule base 58 on a support 60, which is formed as a shoulder 60 of the resilient insert 50. At the upper side, a hollow cylinder 62 made of a gas-permeable foam material and which is secured to the inner side of the housing 19 pushes the glass ampoule 54 against the support 60. Openings are provided between the hollow cylinder 52 and the housing 19, through which openings air or gas from the surroundings of the receptacle 2 and the vacuum mixing device can flow into the receptacle 2. The monomer liquid can thus flow out from the receptacle 2 more easily. The openings between the hollow cylinder 52 and the housing 19 are formed in such a way that they are arranged in the lateral cylinder wall of the hollow cylinder 52 in a manner bordering the upper base area of the hollow cylinder 52. The hollow cylinder 52 thus bears only in regions against the housing 19. Air can flow therebetween into the interior of the receptacle 2.

In the region of the ampoule base 58 or the support 60, the hollow cylinder 52 has a recess, within which the edge 48 bears against the resilient insert 50, such that the ampoule base 58 is broken open by the opening device 5 and therefore the glass ampoule 54 can be opened. The ampoule head 56 of the glass ampoule 54 is usually broken open in order to open the glass ampoule 54. Since the glass ampoule 54 is thin at the neck, this means that the monomer liquid can run out only slowly from the glass ampoule 54 and therefore the user must wait until they can perform the next steps for operating the vacuum mixing device. This is not suitable in the case of the largely automated method, which is driven by operation of the lever 4 or the operating element 4, since it is not possible to ensure that the monomer liquid from the glass ampoule 54 will be available yet when the pump 3 is driven via the operating element 4.

The glass ampoule 54 pushes into the insert 50 made of the deformable material. The insert 50 together with the hollow cylinder 52 forms the essential parts of the receptacle 2 for the glass ampoule 54. The glass ampoule 54 can be pushed into the insert 50 of the liquid container 2 only as far as the ampoule base 58 on account of the shoulder 60.

The liquid container 2 has a lateral opening, in which the insert 50 forms a deformable side wall. At this point, the glass ampoule 54 can be opened or broken open by application of a pressure onto the glass ampoule 54 by the deformable side wall 50 just above the ampoule base 58. When the ampoule base 58 of the glass ampoule 54 is broken open or the glass ampoule 54 is opened, the monomer liquid can flow out from the open glass ampoule 54 over the entire cross-section, such that the monomer liquid is quickly available in its entirety for further processing within the vacuum mixing device.

In order to deform the deformable side wall 50 and thus break open the glass ampoule 54, the lever 42 is used, which can be operated via the lever 4 and which can be rotated about the axis 40. The lever 4 is mounted pivotably or rotatably about the axis 40 relative to the housing 19. The axis 40 divides the lever 4 into a long lever arm 41, to which the handle 44 is secured, and a short lever arm 42, which is arranged inside the housing 19. At the start, the long lever arm 41 can only be moved away from the liquid container 2 and not towards said container, since the long lever arm 41 bears at the top against the opening of the housing 19 and thus prevents a further movement in this direction.

The short lever arm 42 of the lever 4 bears on its side facing towards the liquid container 2 against the lever 46 of the opening device 5, which is connected to the base part 18 or the housing 19 of the vacuum mixing device via a joint 47 or the axis 47 in a manner rotatable about the axis 47. This lever 46 of the opening device 5 is arranged inside the housing 19. The free lever end of the lever 46 in the housing 19 is movable by means of the short lever arm 42. At the tip of the free lever end, the edge 48 is secured and bears against the deformable side wall 5. The axis 47 of the lever 46 is arranged here such that the free lever arm and therefore the edge 48 moves in the direction of the deformable side wall 5 and in the direction of the base part 18. The force that can be exerted from the edge 48 through the deformable side wall 50 onto the glass ampoule 54 thus also pushes the glass ampoule 54 lightly in the direction of the shoulder 60 and thus presses the glass ampoule 50 into the receptacle 2.

A sieve 64 and/or a filter 64 are/is arranged below the shoulder 60, by means of which sieve and/or filter glass splinters of the opened or broken-open glass ampoule 54 are held back. The distance between the shoulder 60 and the sieve 64 and/or filter 64 is greater than the outer diameter of the glass ampoule 54, such that the dropping ampoule base 58 can rotate in the gap and the flow of monomer liquid from the opened glass ampoule 54 is not hindered (see FIGS. 6 to 8). The monomer liquid then remains at least in part in a storage volume 66, which is arranged below the glass ampoule 54 and in which the sieve 64 and/or the filter 64 are/is arranged. A funnel 68 is arranged below the sieve 54 and/or filter 64 and opens out into a fluid connection 70 or liquid line 70.

The front side of the cartridge 6 (at the bottom in FIGS. 1 to 4 and 6 to 8) is tightly connected to the storage volume 66 or the funnel 68 of the liquid container 2 by the base part 18 and the housing 19 via the fluid connection 70. A loop 71 is provided in the fluid connection 70, by means of which a monomer liquid (not shown) contained in the liquid container 2 or the storage volume 66 is prevented from being able to advance undesirably into the interior of the cartridge 6.

The cartridge 6 is releasably secured perpendicularly on the housing 19. The fluid connection 70 opens out in the connection piece having the external thread 16 through a filter 72 impermeable to powder but permeable for the monomer liquid into the interior of the cartridge 6. An annular channel 73 (denoted only in FIGS. 3 and 8, but also visible in FIGS. 4, 6 and 7) is formed beneath the filter 72 and is open towards the filter 72, such that the filter 72, which is likewise annular, covers the annular channel. The annular channel 73, into which the fluid connection 70 opens out and which strictly speaking also belongs to the fluid connection 70, and the annular filter 72 surround the passage in which the mixing shaft 12 or the cable 12 is guided in the interior of the cartridge 6. Seals (not shown) or at least scrapers (not shown) can be provided in the passage for this purpose. As a result of the annular channel 73, the monomer liquid is introduced through the filter 72 around the mixing shaft 12 into the interior of the cartridge 6. A nozzle (not shown) can also be provided at the entry of the fluid connection 70 into the interior of the cartridge 6, which nozzle distributes the monomer liquid in the interior or in the cement powder 9.

The liquid container 2 is closed upwardly by means of the housing 19 once the glass ampoule 54 has been inserted into the liquid container 2. So that the monomer liquid can run out or run off from the glass ampoule 54 and the storage volume 66 without difficulty, a number of passages (not shown) can additionally be provided in the part of the housing 19 covering the liquid container 2, through which air from outside can flow into the liquid container 2. Once the glass ampoule 54 has been broken open, the monomer liquid is available in the storage volume 66 and the fluid connection 70 and can be conducted through the fluid connection 70 into the interior of the cartridge 6, in which a negative pressure in the interior of the cartridge 6 is used in order to suck the monomer liquid from the liquid container 2 into the interior of the cartridge 6. This negative pressure is generated by means of the pump 3. In the interior of the cartridge 6, the monomer liquid can then be mixed with the cement powder 9 with the aid of the mixing device 10 under vacuum or under negative pressure in order to produce the bone cement 96 or a bone cement dough 96.

The mixing device 10 is used to mix the content in the interior of the cartridge 6. The cable 12 or the mixing shaft 12, via which the mixing device 10 is rotated in the interior and is moved up and down in the longitudinal direction of the interior, is deflected via pins 74 or deflection rollers 74 in the direction of a cylinder 76. The deflection rollers 74 can be reconstructed with spring-mounted tubes or deflection sleeves. Here, the springs serve merely to fix the deflection rollers 74 or deflection sleeves. The cable 12 or the mixing shaft 12 is rigidly connected to the cylinder 76. The cylinder 76 has a steep external thread 78 on the outer side. The cylinder 76 is arranged in a sleeve 80 having an internal thread 82 matching the external thread 78. As the cylinder 76 is moved in the sleeve 80 in the longitudinal direction (of the cylinder axis), the mixing device 10 is thus moved via the cable 12 or the mixing shaft 12 in the longitudinal direction of the interior of the cartridge 6 and at the same time is rotated about the mixing shaft 12 on account of the threads 78, 82, and the content in the interior is thus mixed. Alternatively to the external thread 78 on the sleeve, one or more protrusions or one or more lobes 78 can also be provided, which run in the internal thread 82 and thus rotate the cylinder 76 in the sleeve 80.

The cylinder 76 is connected via a ball joint or a ball joint head 84 to a rigid cable 86 or a flexible rod 86, which is constructed similarly to the cable 34 or the flexible rod 34 for the pump 3. The ball joint head 84 can thus move within a receptacle for the ball joint head 84 of the cylinder 76 and can rotate therein. It is thus made possible, as the cable 86 moves, for a rotation of the cylinder 76 in the sleeve 80 to be enforced at the same time. The cable 86, which is connected to the cylinder 76, and the cable 34, which is connected to the plunger 30 of the pump 3, are connected to one another, wherein both are positioned via pins 88 or deflection rollers 88. The defection rollers 88 are constructed similarly to the deflection rollers 74. The connection of the cable 34 to the plunger 30 can also be constructed by means of a ball joint. The two cables 34, 86 or flexible rods 34, 86 are joined together to form a cable 90 or a flexible rod 90 which is guided upwardly to the lever 4 or to the operating element 4, wherein the cable 90 or the flexible rod 90 ends there in the detent means 36. The cable 90 is also constructed similarly to the cable 34 for the pump 3, or the flexible rod 90 is constructed similarly to the flexible rod 34 for the pump 3. The cables 34, 86, 90 connected in a forked manner or the forked rods 34, 86, 90 can be produced from a plastics material by injection moulding, or the common forked cable 34, 86, 90 or the forked rod 34, 86, 90 can be produced from a plastics material by injection moulding. The detent means 36 at the end of the cable 90 is mounted here and pretensioned such that it engages with the mating detent means 38 and latches therewith when the lever 4 is rotated or pivoted or when the mating detent means 38 is pivoted at the height of the detent means 36.

The maximum stroke, which is determined by a rounded portion on the lever 4 formed as an involute 83, the cable 90 or the flexible rod 90 being brought up to the involute 83 following successful latching, is sufficient for the mixing device 10 to be passed through the interior of the cartridge 6 over the entire length thereof. This can be seen in FIGS. 3, 4, 6 and 7 in comparison with FIG. 8, since with a complete stroke of the lever 4, which is illustrated in FIG. 8, the mixing device 10 or the mixing blades 10 bears/bear on the filter 72 at the front side of the interior of the cartridge 6, whereas without stroke, as illustrated in FIG. 7, the mixing device 10 or the mixing blades 10 bears/bear against the dispensing plunger 8 or the sterilisation plunger 22 and the pore plate 24 on the rear side of the interior of the cartridge 6. A complete mixing of the interior of the cartridge 6 with the mixing device 10 is thus made possible. The mating detent means 38 is for this purpose arranged at the end of the involute 83 facing away from the pulling direction of the cables 90, 34, 86 or the flexible rods 90, 34, 86 so that the cable 90 or the flexible rod 90 can be brought up over a wide area of the involute 83.

Instead of connecting the cable 34 or other flexible rod 34 of the pump 3 and the cable 86 or flexible rod 86 of the cylinder 76 to one another to form the cable 90 or the flexible rod 90, on which the detent means 36 is arranged, each of the cables 34, 86 or each of the flexible rods 34, 86 can just as easily have its own detent means, which engages with the mating detent means 38 or the two different mating detent means at the end of the involute 83 or the lever 4 and latches therewith.

In an alternative embodiment of a mixing device according to the invention, the cable 12 can be directly connected to the cable 86, or the two cables 12, 86 can be formed as a common continuous cable, or the flexible rod 12 can be formed in one part with the flexible rod 86. The cylinder 76, the sleeve 80, and the threads 78, 82 are then superfluous and are not provided. This leads to the mixing device 10 no longer being rotated by the mixing shaft 12 in the interior of the cartridge 6. A mixing of the interior of the cartridge 6 is then still achieved only by the movement up and down of the mixing device 10 in the longitudinal direction. By means of a suitable inclination of the mixing blades 10 or some of the mixing blades 10 and/or by a guidance of at least one protrusion (not shown) on the mixing device 10 in at least one spiralled groove (not shown) in the inner wall of the cartridge 6, a rotation of the mixing device 10 in the cartridge 6 can also be enforced in another way, provided the rotation of the mixing device 10 in the cartridge 6 is not easily foregone.

FIG. 5 shows a schematic cross-sectional view of the vacuum mixing device according to FIGS. 1 to 4 and 6 to 8 with a plane of section perpendicular to the section in FIGS. 3 and 4 and 6 to 8. Inter alia, an exemplary construction of the check valves 27, 28 is explained herein. The check valves 27, 28 are constructed with balls 91, which are pushed by springs 92 onto a ball seat, in which the connection to the vacuum line 26 or to the surroundings of the pump 3 is disposed. When the balls 91 are pushed onto the ball seat, these connections are closed. The check valve 27 opens when a negative pressure relative to the pressure in the vacuum line 26 or relative to the interior of the cartridge 6 is created or provided in the pump 3 by moving the plunger 30 in the direction of the closure 33, i.e. when the pump chamber 94 (see FIG. 8) opens. The check valve 28 by contrast opens when a pressure greater than that in the surroundings prevails in the pump chamber 94 or in the pump 3. Otherwise, the check valves 27, 28 close on account of the spring force of the springs 92.

Figure 2:
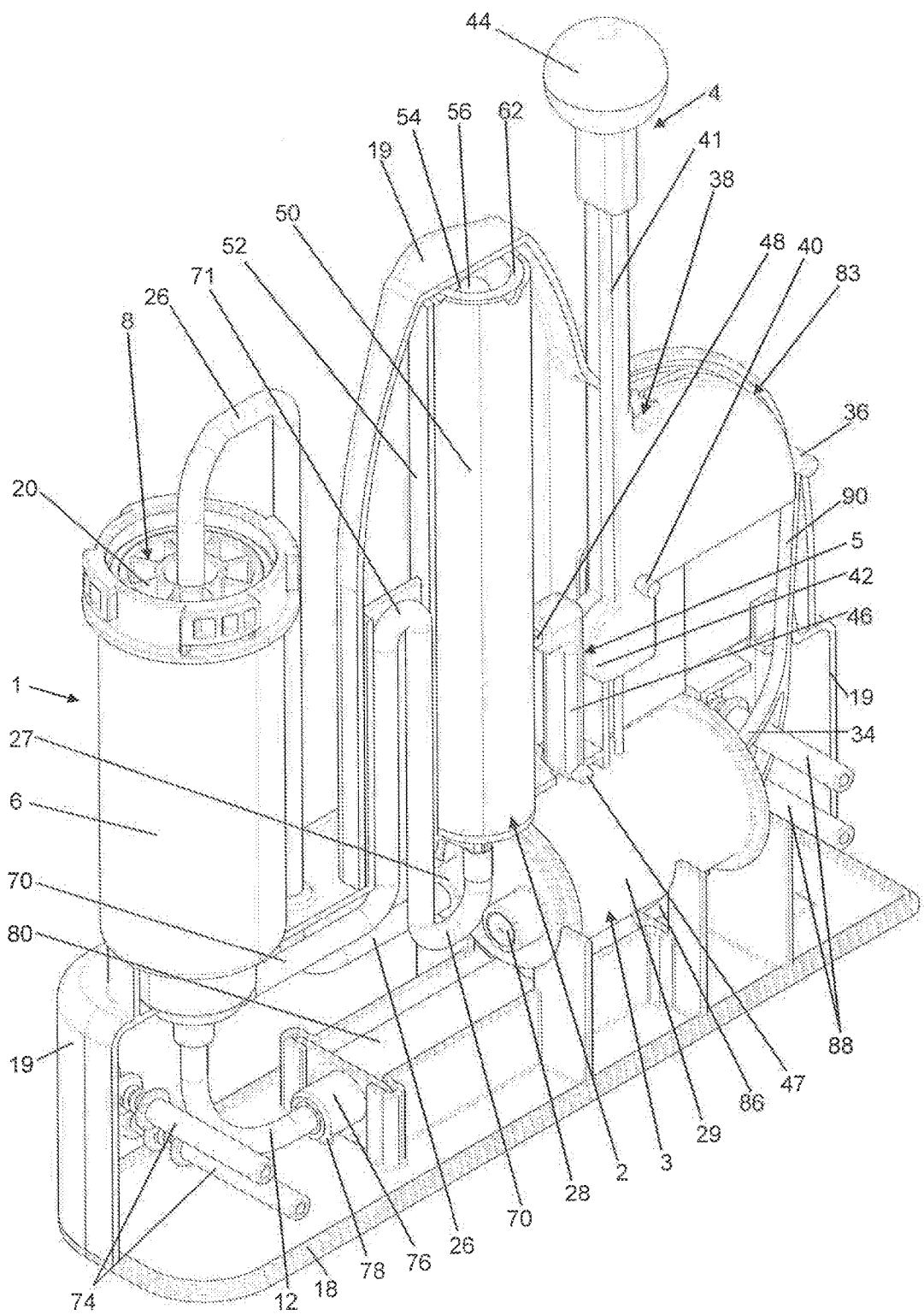
FIG. 2: shows a schematic perspective view of the vacuum mixing device according to FIG. 1 with open housing.
Figure 3:
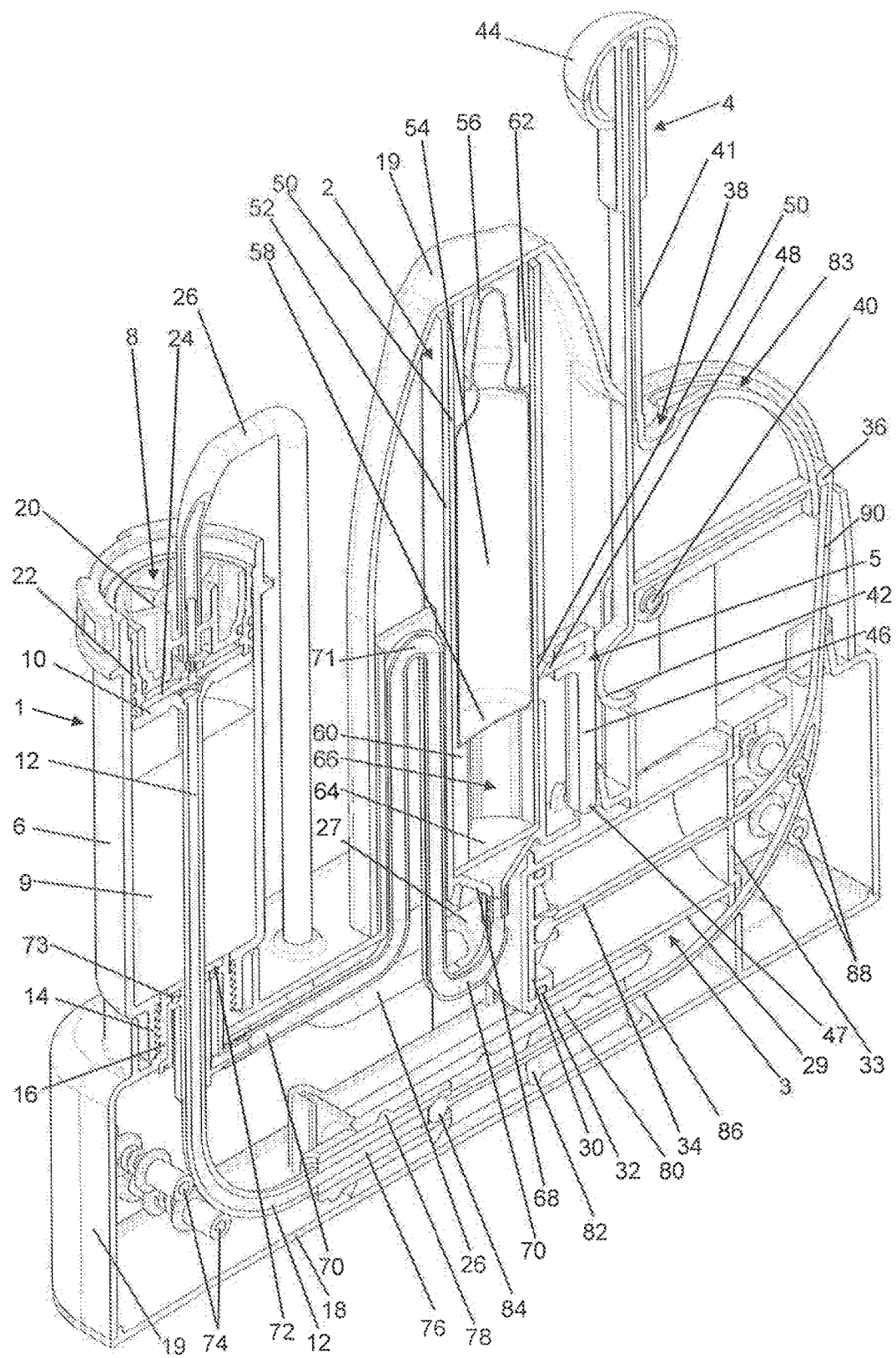
FIG. 3: shows a schematic perspective cross-sectional view of the vacuum mixing device according to FIGS. 1 and 2 in the starting state.
Figure 4:
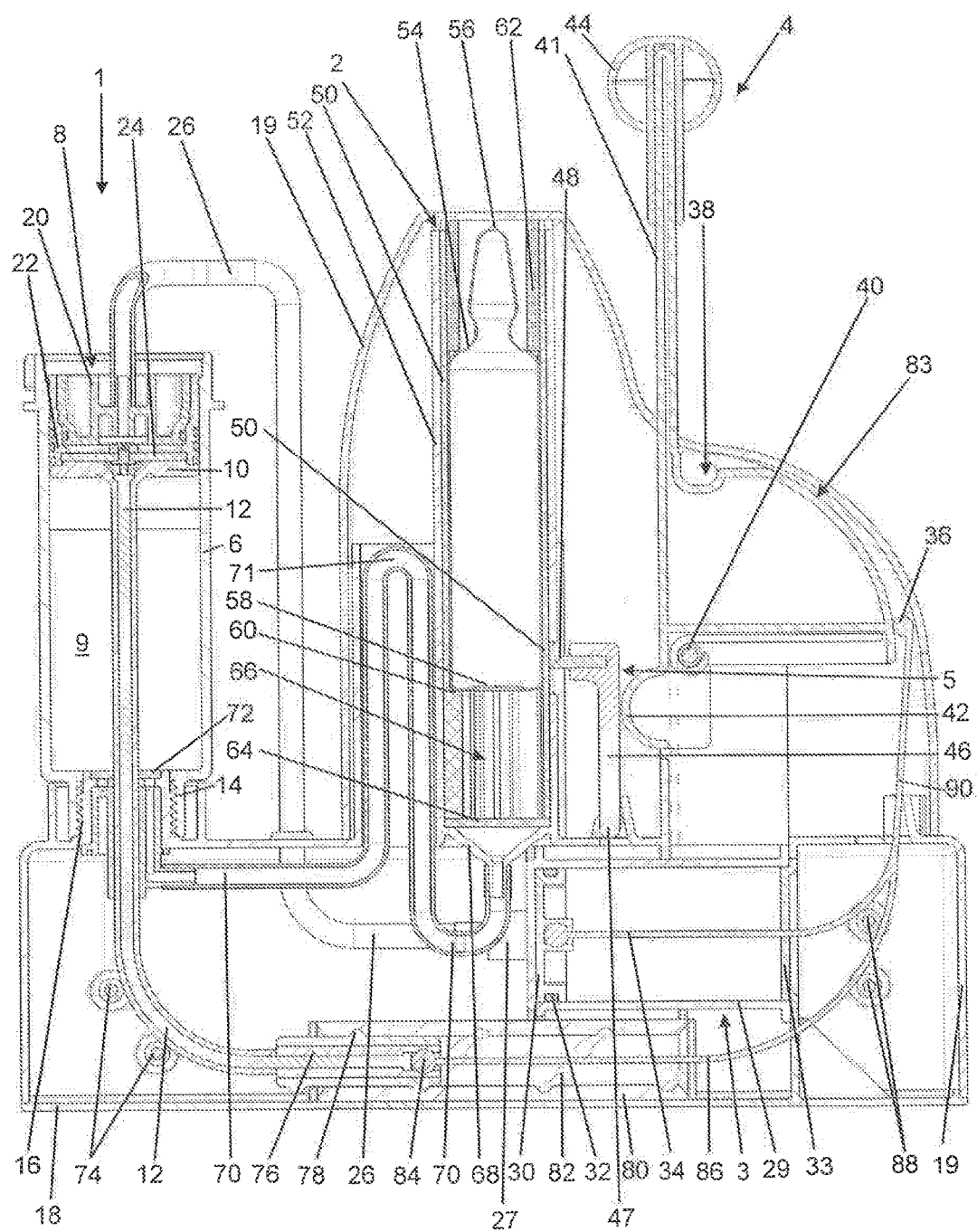
FIG. 4: shows a schematic cross-sectional view of the vacuum mixing device according to FIGS. 1 to 3 in the starting state.

The vacuum mixing device is characterised in accordance with the invention by the applicability of the following exemplary method according to the invention. The monomer liquid is provided in the liquid container 2 by breaking open the glass ampoule 54 by means of the opening device 5, as explained above. For this purpose, the lever 4, which is disposed originally in an upright position (see FIGS. 1 to 4) is pushed down (see FIG. 6). Whilst the monomer liquid runs out and fills the storage volume 66 and the fluid connection 70, without passing via the loop 71, the lever 40 is rotated or pivoted further, until the mating detent means 38 is rotated at the height of the detent means 36 and both latch with one another (see FIG. 7). By means of the latching of the detent means 36 with the mating detent means 38, the pump 3 can now be moved or driven by means of the lever 4 via the cable 34, 90 or the flexible rod 34, 90, and the mixing device 10 can be driven by means of the lever 4 via the cable 86, 90 or the rod 86, 90, the cylinder 76, and the cable 12 or the mixing shaft 12. For this purpose, the lever 4 is rotated or pivoted away from the lower stop, back into the starting position (FIGS. 2 to 4).

The pump 3 is used in that the plunger 30 is drawn by means of the operating element 4 via the cable 34, 90 or the flexible rod 34, 90 away from the check valves 27, 28 in the direction of the closure 33. In so doing, the pump chamber 94 inside the pump 3 opens (see FIG. 8). Due to the enlargement of the pump chamber 94, a lower pressure is generated in the pump chamber 94. This leads to an opening of the check valve 27, so that gas is sucked or pushed from the interior of the cartridge 6, through the connection line 26, into the pump chamber 94. On account of the resultant negative pressure, the monomer liquid is sucked from the storage volume 66, through the fluid connection 70, into the interior of the cartridge 6.

The plunger 30 is moved as far as the end of the hollow cylinder 29 (on the right in FIGS. 3 to 4 and 6 to 8). This arrangement is shown in FIG. 8. The volume increase of the pump chamber 96 can preferably be sufficient to evacuate the gas from the vacuum line 26, the interior of the cartridge 6, and the fluid connection 70, and to draw the monomer liquid from the liquid container 2 into the interior of the cartridge 6, such that just one stroke of the plunger 30 is sufficient to transfer the monomer liquid into the interior of the cartridge 6. The expanded pump chamber 96 for this purpose can preferably be larger than the volumes of the lines 26, 70, the interior of the cartridge 6, and the liquid volume of the monomer liquid. Due to the negative pressure in the interior of the cartridge 6, the monomer liquid is sucked away from the receptacle 2 or the storage volume 66, through the fluid connection 70, via the loop 71, into the interior of the cartridge 6. Alternatively to the transfer of the monomer liquid by means of a single stroke of the plunger 30, however, the monomer liquid can also be sucked into the interior of the cartridge 6 by means of a number of strokes of the plunger 30 by repeated operation of the lever 4 (pivoting of the lever 4 to and fro).

The part of the interior of the hollow cylinder 29 between the front closure with the check valves 27, 28 thereon (on the left in FIGS. 3, 4 and 6 to 8, and at the top in FIG. 5) and the plunger 30 forms the pump chamber 94. A negative pressure in the pump chamber 94 can thus act through the vacuum line 26 into the interior of the cartridge 6, or a gas can be evacuated from the interior of the cartridge 6 when the sealing plunger 20, as shown in the Figures, is connected to the sterilisation plunger 22 and the interior of the cartridge 6 is thus sealed externally, apart from the opening to the vacuum line 26.

At the same time as the continued movement of the plunger 30, the cylinder 76 in the sleeve 80 is moved in the longitudinal direction via the cable 86, 90 or the rod 86, 90 and the ball joint 84, and, in so doing, is rotated via the threads 72, 82. The movement in the longitudinal direction and the rotation is transferred via the mixing shaft 12 or the cable 12 through the feedthrough onto the mixing device 10 in the interior of the cartridge 6. As a result of multiple pivoting of the lever 4 in both directions and thus movement of the mixing device 10 in the interior of the cartridge 6, the content, specifically the bone cement powder 9 and the sucked-in monomer liquid, is mixed, thereby producing a bone cement dough 96 in the interior of the cartridge 6.

When the starting components have been mixed in the interior of the cartridge 6 by means of the mixing blades 10, the cartridge system 1 is unscrewed from the housing 19 or the external thread 16 of the housing 19, and the cable 12 or the mixing shaft 12 comprising the mixing device 10 is removed from the interior of the cartridge 6. In so doing, the mixing blades 10 collapse upwardly. For this purpose, tapered material portions as predetermined bending points are provided at the point of connection of the mixing blades 10 to the mixing shaft 12.

The sealing plunger 20 is rotated relative to the sterilisation plunger 22, and the gas feedthrough is thus closed by the sealing plunger 20. The vacuum line 26 is removed from the sealing plunger 20. Once the cartridge system 1 has been unscrewed, a dispensing pipe (not shown) having a matching external thread is screwed into the internal thread 14, and the mixed bone cement 96 can be applied through said pipe. The conveying plunger 8 or dispensing plunger 8 assembled from the sterilisation plunger 22 and the sealing plunger 20 is unlatched and can be driven inside the cartridge 6 by means of an application device (not shown). The content in the cartridge 6, i.e. the bone cement dough 96 mixed under negative pressure, is thus pressed out from the opposite opening and through the screwed-on dispensing pipe.

The components of the vacuum mixing device, apart from the glass ampoule 54, the filters 64, 72, and the starting components of the bone cement, can be produced from plastics material by injection moulding. The fluid connection 70 can consist of another plastics material. The connection line 26 can be flexible so as to be able to be removed more easily from the sealing plunger 20.

The lines 26, 70 and the cables 34, 86, 90 or the forked rod 34, 86, 90 are arranged in the housing 19 made of plastics material, which is fixedly connected to the base part 18, wherein the base part 18 has a flat base so that the vacuum mixing device can be placed on a flat substrate.

Instead of the glass ampoule 54 used with the exemplary embodiment described, another monomer liquid container can also be used. By way of example, a film bag containing the monomer liquid can be used as container for the monomer liquid in a modified receptacle. The film bag by way of example can be a plastics material bag coated with aluminium which is chemically sufficiently resistant to the monomer liquid. In the alternative receptacle 2, a mandrel or better still a blade can be provided, which is to be pushed and moved against the film bag by means of the opening device 5 so that the film bag is pierced or slit open by means of the mandrel or the blade via the opening device 5, such that the monomer liquid then runs out from the film bag and is available in the receptacle 2. The container for the monomer liquid can also be fixedly integrated in the receptacle 2 and therefore in the vacuum mixing device and can be opened towards the filter 64 and/or sieve 64 or towards the fluid connection 70 by means of the opening device 5.

The variant with glass ampoule 54 as container for the monomer liquid is preferred, however, in accordance with the invention, since the glass ampoules 54 filled with monomer liquid are commercially available inexpensively and in addition glass ampoules 54 are particularly well suited for long-term storage of the monomer liquid. Here, it is particularly preferred for the glass ampoule 54 to be contained already in the receptacle 2 of the vacuum mixing device.

With the described vacuum mixing device, the two starting components of the bone cement can be stored and mixed at any later moment in time under vacuum. Here, the vacuum mixing device does not have to be connected to an external supply (power, water or compressed gas). There is no need for an internal energy store, such as a battery, a compressed gas cartridge or a tension spring, for driving the vacuum mixing device or the pump 3, the mixing device 10, and the opening device 5. The energy necessary to generate the negative pressure is also applied manually, such as the force necessary to open the glass ampoule 54 and the force necessary to move the mixing device 10.

The features of the invention disclosed in the above description and in the claims, Figures and exemplary embodiments can be essential, both individually and in any combination, for the implementation of the invention in its various embodiments.

LIST OF REFERENCE SIGNS

1 cartridge system
2 receptacle
3 pump
4 operating element/lever
5 opening device
6 cartridge/cartridge wall/hollow cylinder
8 dispensing plunger
9 cement powder
10 mixing device/mixing blades
12 mixing shaft/cable
14 internal thread
16 external thread
18 base part/stand
19 housing
20 sealing plunger
22 sterilisation plunger
24 pore plate
26 connection line/vacuum line
27 check valve
28 check valve/exhaust air
29 hollow cylinder
30 plunger
32 seal/O-ring
33 closure
34 cable/flexible rod
36 detent means
38 mating detent means
40 axis
41 lever arm
42 lever arm
44 handle
46 lever
47 axis
48 edge
50 resilient insert
52 hollow cylinder
54 glass ampoule with monomer liquid
56 ampoule head
58 ampoule base
60 support/shoulder
62 hollow cylinder
64 filter/sieve
66 storage volume
68 funnel
70 fluid connection/liquid line
71 loop
72 powder-impermeable and liquid-permeable filter
73 annular channel
74 pin/deflection roller
76 cylinder
78 external thread/lobe
80 sleeve
82 internal thread
83 involute
84 ball-joint head
86 cable/flexible rod
88 pin/deflection roller
90 cable/flexible rod
91 ball
92 spring
94 pump chamber
96 bone cement dough

We claim:

1. A vacuum mixing device for mixing polymethylmethacrylate bone cement from a monomer liquid and a cement powder, the vacuum mixing device comprising
- at least one cartridge comprising an evacuable interior for mixing of the bone cement,
- a mixing device for mixing the content in the interior of the at least one cartridge, which is arranged movably in the interior,
- a receptacle for receiving a separate container containing the monomer liquid or comprising an integrated container containing the monomer liquid, an opening device, that is arranged in the region of the receptacle in a manner movable relative to the receptacle such that, by moving the opening device, a separate container arranged in the receptacle is openable by means of the opening device, or the opening device is arranged in the region of the integrated container in a manner movable relative to the integrated container so that, by moving the opening device, the integrated container is openable by means of the opening device,
- a pump, in which a movable plunger for generating a negative pressure is arranged and delimits a pump chamber of the pump, and
- a connection line, which connects the interior of the at least one cartridge to the pump chamber of the pump, wherein
- the vacuum mixing system comprises an operating element that is operatable from outside, wherein the plunger in the pump is movable manually by means of the operating element, and further wherein
- the opening device is movable relative to the receptacle or relative to the integrated container by means of the same operating element, and
- the mixing device in the interior of the cartridge is movable by means of the same operating element in order to mix the content in the interior of the cartridge.

2. The vacuum mixing device according to claim 1, wherein the operating element is connected, or is connectable, to the plunger such that the plunger is movable manually in the pump by operation of the operating element.

3. The vacuum mixing device according to claim 1, wherein the receptacle, at least in regions, has closed side walls for receiving a glass ampoule as separate container, wherein the receptacle has at least one deformable closed side wall and a supporting element is provided opposite the deformable side wall, wherein the opening device is pressable via the operating element against the deformable side wall of the receptacle so that the deformable side wall deforms such that a matching glass ampoule arranged in the receptacle can be broken open by means of the opening device.

4. The vacuum mixing device according to claim 1, wherein the opening device has a first lever which is mounted rotatably about a first axis in relation to the receptacle or the integrated container, wherein a free end of the first lever is pushable against a deformable side wall of the receptacle or the integrated container, wherein the operating element is formed by a second lever, which is mounted rotatably about a second axis in relation to the receptacle or the integrated container, wherein the second axis divides the second lever into a short lever arm and a long lever arm, wherein an end of the short lever arm is to be pushed by manual operation of the long lever arm against the first lever so that the free end of the first lever pushes against the deformable side wall and deforms this in such a way that a separate container disposed in the receptacle is openable, or pushes the first end of the first lever against the integrated container so that the integrated container opens towards a fluid connection.

5. The vacuum mixing device according to claim 1, wherein the operating element is manually movable about an axis, wherein the operating element (4) is operatively connected to or is to be brought into operative connection with the opening device, the pump, and the mixing device such that a first operation of the operating element, and with a further operation of the operating element, the plunger in the pump is to be driven, and the mixing device in the interior is to be driven.

6. The vacuum mixing device according to claim 5, wherein the plunger of the pump and/or the mixing device are/is to be driven via a flexible cable and/or a rod, wherein a detent means is provided on the flexible cable and/or the rod and after first-time operation of the operating element engages with a mating detent means on the operating element or with a mating detent means connected to the operating element so that, with operation of the operating element subsequent to the latching, the plunger of the pump and/or the mixing device are/is to be driven via the cable and/or the rod by means of the operating element.

7. The vacuum mixing device according to claim 1, wherein the mixing device is axially movable in the interior in the longitudinal direction by operation of the operating element.

8. The vacuum mixing device according to claim 1, wherein the mixing device is rotatable about the longitudinal axis of the interior by operation of the operating element, wherein for this purpose a cylinder connected to the mixing device and having an external thread moves in a stationary sleeve having a matching internal thread so that, when the cylinder moves along the longitudinal direction within the sleeve, a rotation of the cylinder is enforced, wherein the rotation of the cylinder transfers to the mixing device in the interior of the cartridge.

9. The vacuum mixing device according to claim 1, wherein the pump chamber of the pump is gas-tight and is arranged in the interior of the pump, wherein the plunger is manually drivable via the operating element in at least one direction, such that the pump chamber is to be enlarged by the movement of the plunger and the interior of the at least one cartridge is to be evacuable through the connection line by means of the resultant negative pressure created in the pump chamber.

10. The vacuum mixing device according to claim 1, wherein a first one-way valve is arranged in the connection from the pump chamber to the connection line or in the connection line, which first one-way valve is open or is actively opened when a pressure lower than in the interior of the cartridge prevails in the pump chamber and is in a closed state or is actively closed when a pressure equal to or higher than in the interior of the cartridge prevails in the pump chamber, and a second one-way valve connects the pump chamber to the surroundings of the pump, which second one-way valve is open or is actively opened when a pressure higher than in the surroundings of the pump prevails in the pump chamber and is in the closed state or is actively closed when a pressure equal to or lower than in the surroundings of the pump prevails in the pump chamber.

11. The vacuum mixing device according to claim 1, wherein the plunger is mounted axially movably in a hollow cylinder, wherein the hollow cylinder is closed on a first side or is closed apart from a feedthrough for a rod or cable connected to the operating element and the plunger, in particular is closed by a closure, wherein a pump chamber is formed in the hollow cylinder between the plunger and the first closed side, wherein the hollow cylinder is open on a second side.

12. The vacuum mixing device according to claim 1, wherein the plunger is connected or is connectable via a rod and/or a cable to the operating element, and the plunger preferably is to be moved in the pump by operation of the operating element.

13. The vacuum mixing device according to claim 1, wherein a movable dispensing plunger for discharging the mixed bone cement from the cartridge is arranged in the interior of the cartridge, wherein the dispensing plunger is preferably releasably locked or is lockable in order to prevent a movement of the dispensing plunger under the action of the negative pressure.

14. The vacuum mixing device according to claim 1, wherein the cartridge is a cement cartridge filled with cement powder and a separate container containing a monomer liquid is arranged in the receptacle or a monomer liquid is contained in the integrated container, wherein the receptacle or the integrated container is preferably connected in a liquid-impermeable manner to the interior of the cement cartridge by means of a separating element that is to be opened and/or the interior of the cement cartridge is connected or connectable in a gas-permeable manner to the pump.

15. The vacuum mixing device according to claim 1, wherein the cartridge, the pump, and all lines and also the receptacle or the integrated container are fixedly and/or releasably connected to a common base part and/or a housing, wherein the pump and all lines as well as the receptacle or the separate container are preferably fixedly connected to the base part and/or a housing and the cartridge is releasably connected to the base part and/or a housing.

16. The vacuum mixing device according to claim 1, wherein the separate container containing the monomer liquid is a film bag which can be cut open or torn open in the receptacle by means of the opening device, or is a glass ampoule which can be broken open in the receptacle by means of the opening device.

17. The vacuum mixing device according to claim 1, wherein the receptacle or the integrated container is connected or connectable via a fluid connection to the interior of the cartridge, wherein the mouth of the fluid connection into the interior of the cartridge is arranged on the opposite side of the mouth of the connection line between the interior and the pump chamber.

18. The vacuum mixing device according to claim 17, wherein a loop is arranged in the fluid connection, such that the monomer liquid running out from the opened separate container or the integrated container cannot flow into the interior of the cartridge without negative pressure in the interior of the cartridge, wherein a storage volume for receiving the liquid volume of the monomer liquid is preferably arranged below the receptacle or the integrated container.

19. The vacuum mixing device according to claim 1, wherein a negative pressure is to be generated in the pump chamber as a result of the movement of the plunger in the pump, wherein a gas is evacuable through the connection line from the interior of the at least one cartridge by means of the negative pressure.

20. The vacuum mixing device according to claim 1, wherein the pump is constructed with a hollow cylinder, wherein the hollow cylinder is connected or connectable to the interior of the cartridge, a gas-tight closure at one hollow cylinder end, the plunger, which is arranged in the hollow cylinder in a gas-tight and actually movable manner, wherein the plunger in the pump is movable by means of the manually operable operating element, wherein with a movement of the plunger by means of the manually operable operating element, the plunger is movable axially oppositely to the closure and gas can thus be evacuated from the interior of the cartridge, wherein, the operating element is operatively connected to the opening device, and wherein the operating element is connected to the mixing device in the interior of the cartridge in such a way that the mixing device in the interior of the cartridge is movable with operation of the operating element.

21. The vacuum mixing device according to claim 1, wherein the pump, the opening device, and the mixing device are drivable via the movement of the operating element, wherein the operating element is preferably moved by the action of manual force.

22. A method for mixing polymethylmethacrylate bone cement in an interior of a cartridge of the vacuum mixing device according to claim 1, the method comprising:
operating the operating element and an integrated container of the vacuum mixing device or a separate container, which is arranged in a receptacle of the vacuum mixing device, is thus opened, wherein a monomer liquid contained in the integrated container or the separate container then runs out as first component of the bone cement, by means of a subsequent, further operation of the operating element, a movement of a plunger of a pump of the vacuum mixing device is driven, wherein a negative pressure is generated in a pump chamber of the pump by means of the movement of the plunger, wherein the interior of the cartridge is evacuated by means of the pump driven in this way and the monomer liquid is conducted into the interior of the cartridge by means of the negative pressure in the interior of the cartridge, wherein a bone cement powder as second component of the bone cement is already disposed in the interior of the cartridge; and
moving a mixing device in the interior of the cartridge is moved as a result of the operation of the operating element and a bone cement dough in the interior of the cartridge formed from the cement powder and the monomer liquid is mixed as a result of the movement of the mixing device.

23. The method according to claim 22, wherein the volume of a pump chamber of the pump is increased by the manual movement of the plunger and the interior of the cartridge is evacuated due to the negative pressure created as a result.

24. The method according to claim 22, wherein the plunger of the pump is moved by means of the operating element, whereby a negative pressure relative to the surrounding atmosphere is generated in the pump, in so doing gas from the interior of the cartridge is sucked into the pump chamber of the pump through a connection line, and the mixing device in the interior of the cartridge is then moved by operation of the same operating element, and in so doing the cement powder is mixed with the monomer liquid, the cartridge containing the mixed cement dough is then removed, and the cement dough is pressed out from the cartridge by means of an axial movement of a dispensing plunger.

25. The method according to claim 22, wherein the cement powder is arranged in the cartridge, the monomer liquid is arranged in a receptacle separate from the cartridge, wherein the monomer liquid is contained in an integrated container or in a separate container, preferably in a glass ampoule in the receptacle, the integrated container or the separate container is opened by operation of the operating element and a resultant movement of the opening device, before the plunger is driven by a further operation of the operating element, the plunger is then moved axially in a hollow cylinder, whereby a negative pressure compared to the surrounding atmosphere is generated, in so doing gas from the interior of the cartridge is sucked through the connection line into the hollow cylinder, and monomer liquid is sucked into the cartridge by means of the negative pressure formed in the interior of the cartridge.

* * * * *